(12) United States Patent
Merritt et al.

(10) Patent No.: US 11,436,284 B1
(45) Date of Patent: Sep. 6, 2022

(54) SYSTEMS AND METHODS FOR COMPUTATIONAL RISK SCORING BASED UPON MACHINE LEARNING

(71) Applicant: MASSACHUSETTS MUTUAL LIFE INSURANCE COMPANY, Springfield, MA (US)

(72) Inventors: Sears Merritt, Groton, MA (US); Michael Bessey, Springfield, MA (US); Marc Maier, Springfield, MA (US)

(73) Assignee: MASSACHUSETTS MUTUAL LIFE INSURANCE COMPANY, Springfield, MA (US)

( * ) Notice: Subject to any disclaimer, the term of this patent is extended or adjusted under 35 U.S.C. 154(b) by 0 days.

(21) Appl. No.: 17/157,808

(22) Filed: Jan. 25, 2021

Related U.S. Application Data

(63) Continuation of application No. 16/404,170, filed on May 6, 2019, now Pat. No. 10,902,065.
(Continued)

(51) Int. Cl.
*G06F 16/904* (2019.01)
*G06F 16/9035* (2019.01)
(Continued)

(52) U.S. Cl.
CPC .......... *G06F 16/904* (2019.01); *G06F 3/0482* (2013.01); *G06F 3/04817* (2013.01);
(Continued)

(58) Field of Classification Search
CPC .. G06F 16/904; G06F 16/9035; G06F 16/252; G06F 16/9024; G06F 3/04817; G06F 3/0482; G16H 50/30; G06N 20/00
See application file for complete search history.

(56) References Cited

U.S. PATENT DOCUMENTS

| | | | |
|---|---|---|---|
| 7,873,567 B2 * | 1/2011 | Eder | G06Q 40/08 705/37 |
| 8,782,217 B1 | 7/2014 | Arone et al. | |

(Continued)

OTHER PUBLICATIONS

Michael Allsop, "Making a Chart with Negative Values Look Good in Excel 2010", published online Oct. 1, 2012 to https://www.wiseowl.co.uk/blog/s311/excel-charts.htm, retrieved Aug. 14, 2021 (Year: 2012).*

(Continued)

*Primary Examiner* — Shourjo Dasgupta
(74) *Attorney, Agent, or Firm* — Foley & Lardner LLP

(57) ABSTRACT

Embodiments disclosed herein disclose a back-end computer to generate a risk score and a front-end visualization engine to hierarchically display the generated risk core. The back-end computer users a machine learning model for a stepwise perturbation from a digital reference profile until a user profile to be score is reached. The computer may calculate intermediate risk score for each perturbation and calculate the final risk score after all the perturbations are completed. The front-end visualization engine generates an interactive hierarchical display showing information associated with the risk score calculation. More specifically, the visualization engine may show a filtered list of users sharing one or more attributes with the user profile, a visual rendering of the top factors contributing to the risk score, and individual input values within a factor; and juxtapose the scores and attributes of the user profile in the graphical information display of the associated population.

20 Claims, 23 Drawing Sheets

Related U.S. Application Data

(60) Provisional application No. 62/667,183, filed on May 4, 2018.

(51) Int. Cl.
| | | |
|---|---|---|
| *G06F 16/25* | (2019.01) | |
| *G06F 16/901* | (2019.01) | |
| *G16H 50/30* | (2018.01) | |
| *G06N 20/00* | (2019.01) | |
| *G06F 3/0482* | (2013.01) | |
| *G06F 3/04817* | (2022.01) | |

(52) U.S. Cl.
CPC ........ *G06F 16/252* (2019.01); *G06F 16/9024* (2019.01); *G06F 16/9035* (2019.01); *G06N 20/00* (2019.01); *G16H 50/30* (2018.01)

(56) References Cited

U.S. PATENT DOCUMENTS

| | | | | |
|---|---|---|---|---|
| 9,141,622 | B1* | 9/2015 | Moore | G06K 9/6277 |
| 10,706,439 | B1* | 7/2020 | Lerner | G06N 20/00 |
| 10,740,793 | B1* | 8/2020 | Sussman | G06Q 30/0255 |
| 11,042,880 | B1* | 6/2021 | Hazan | G06Q 20/4016 |
| 11,182,810 | B1* | 11/2021 | Pandey | G06Q 30/0204 |
| 11,188,940 | B1* | 11/2021 | Vanderveld | G06Q 30/0255 |
| 2006/0173663 | A1 | 8/2006 | Langheier et al. | |
| 2008/0319802 | A1 | 12/2008 | Abraham et al. | |
| 2009/0043637 | A1* | 2/2009 | Eder | G06N 20/00 705/37 |
| 2009/0132347 | A1* | 5/2009 | Anderson | G06Q 30/02 705/30 |
| 2010/0114793 | A1* | 5/2010 | Eder | G06Q 40/08 705/348 |
| 2012/0284207 | A1* | 11/2012 | Eder | G06Q 40/06 705/36 R |
| 2013/0054486 | A1* | 2/2013 | Eder | G06N 7/005 705/36 R |
| 2013/0208977 | A1* | 8/2013 | Jia | G06K 9/6256 382/159 |
| 2013/0332082 | A1* | 12/2013 | Otvos | G01R 33/46 702/19 |
| 2014/0114962 | A1 | 4/2014 | Rosenburg et al. | |
| 2014/0136227 | A1* | 5/2014 | Amland | G16H 50/50 705/2 |
| 2015/0262396 | A1 | 9/2015 | Devarajan et al. | |
| 2016/0055412 | A1* | 2/2016 | Carroll | G16H 50/20 706/46 |
| 2016/0155069 | A1* | 6/2016 | Hoover | G06F 16/26 706/12 |
| 2016/0162802 | A1* | 6/2016 | Chickering | G06N 20/00 706/12 |
| 2016/0225017 | A1* | 8/2016 | Wong | G06Q 10/067 |
| 2016/0239919 | A1* | 8/2016 | Eder | G06Q 40/06 |
| 2017/0018075 | A1* | 1/2017 | Middlebrooks | G06N 20/10 |
| 2017/0018076 | A1* | 1/2017 | Middlebrooks | G06K 9/629 |
| 2017/0132382 | A1* | 5/2017 | Dai | G16H 50/20 |
| 2017/0323326 | A1* | 11/2017 | Kim | G06Q 30/0243 |
| 2018/0019939 | A1* | 1/2018 | Finkelstein | H04W 24/08 |
| 2018/0182471 | A1* | 6/2018 | Yelton | G06F 16/285 |
| 2019/0034830 | A1* | 1/2019 | Burangulov | G06F 16/953 |
| 2020/0250185 | A1* | 8/2020 | Anderson | G06Q 30/01 |

OTHER PUBLICATIONS

"Waterfall Charts", published online Apr. 22, 2010 to https://www.sumproduct.com/thought/waterfall-charts, retrieved Aug. 14, 2021 (Year: 2010).*

Robert Kosara, "Continuous Values and Baselines", published online Apr. 28, 2013 to https://eagereyes.org/basics/baselines, retrieved Aug. 14, 2021 (Year: 2013).*

Amarabha Banerjee, "Iterative Machine Learning: A Step Towards Model Accuracy", published at https://hub.packtpub.com/iterative-machine-learning-step-towards-model-accuracy on Dec. 1, 2017, retrieved Feb. 1, 2022 (Year: 2017).*

Brett Wujek, "Understanding Machine Learning Algorithms", published at https://kdnuggets.com/2017/10/understanding-machine-learning-algorithms.html on Oct. 3, 2017, retrieved Feb. 1, 2022 (Year: 2017).*

Daniel D. Frey, Fredrik Engelhardt, and Edward M. Greitzer, "A Role for One-Factor-At-A-Time Experimentation in Parameter Design", published in Research in Engineering Design 14, pp. 65-74, May 2003, retrieved Feb. 1, 2022 (Year: 2003).*

Sean Salleh, "Sensitivity Analysis: One at a Time or All Together?", published at https://lumina.com/sensitivity-analysis-one-at-a-time-or-all-together on Aug. 16, 2013, retrieved Feb. 1, 2022 (Year: 2013).*

* cited by examiner

US 11,436,284 B1

SYSTEMS AND METHODS FOR COMPUTATIONAL RISK SCORING BASED UPON MACHINE LEARNING

CROSS REFERENCE TO RELATED APPLICATIONS

This application is a continuation application of U.S. patent application Ser. No. 16/404,170, filed May 6, 2019, which claims priority to U.S. Provisional Application No. 62/667,183, filed May 4, 2018, which is hereby incorporated by reference in its entirety.

TECHNICAL FIELD

This application relates generally to computational risk scoring of user databases, and more specifically to using machine learning and statistical models to generate risk scores from data records and visualize the risk scores and their underlying contributing factors in a graphical user interface (GUI).

BACKGROUND

Enterprise level risk scoring based upon multiple data points of complex and interrelated pieces of information is performed by a back-end computer infrastructure. The back-end computer infrastructure pipes in pieces of information from multiple sources, aggregates the received information, and performs risk scoring calculations. These processes performed by the back-end computer infrastructure are inherently computational—the sheer complexity of these processes makes them humanly impossible.

However, the conventional back-end computer infrastructure for computing risk-levels has several technical shortcomings. From an enterprise user's standpoint, the computational risk scoring is a black box process: the enterprise user enters in pieces of information just to see the computer infrastructure produce a result. In other words, the set of scoring rules applied by the back-end infrastructure is abstracted away from the enterprise user. With the advent of machine learning, the set of scoring rules become dynamic, and the back end-computer infrastructure may dynamically apply different set of scoring rules for different types of data, once again, completely black-boxed from the enterprise user. Furthermore, the conventional back-end computer infrastructure does not provide a front-end visualization of the computational risk scoring. Without integrating a front-end visualization and back-end machine learning algorithms, the risk scoring computations remain opaque to the enterprise user. In other words, the conventional back-end computer infrastructure does not provide customization functionality to the enterprise user, wherein the enterprise user may configure the computational risk scoring through front-end interactions with the back-end computer infrastructure.

SUMMARY

What is therefore desired is a back-end machine learning computer infrastructure integrated with a front-end visualization engine, wherein the back-end computer infrastructure computes risk score for user profiles and the visualization engine provides visualization for the risk score computation.

The systems and methods presented herein solve the aforementioned technical problems and may provide solutions to other problems as well. A back-end computer infrastructure may user machine learning algorithms to score user data. More particularly, the computer within the back-end computer infrastructure may train one or more machine learning models from inputs and corresponding known outputs. Furthermore, the computer may generate a digital reference profile for a set of general users having one or more common attributes. When the computer receives input values (also referred to herein as attributes) of a general user, the computer may generate a user profile, grouping the input values to one or more factors within the user profile. The computer may retrieve a corresponding digital reference profile and a corresponding machine learning model to score the user profile. More specifically, the computer may use the machine learning model to generate risk scores via stepwise perturbations of the retrieved digital reference profile until the user profile is reached. The stepwise perturbation is model-agnostic: the computer can use any variety of machine learning or statistical model to start from the digital reference profile and reach the user profile to calculate a risk score for the user profile. At the front-end, a visualization engine may display the scored data in a graphical user interface for the enterprise user to see a detailed and transparent visualization of the contributing factors of the risk score. In addition to the chosen machine-machine learning model, the front-end visualization engine may display a juxtaposition of the risk score of the user profile with a distribution of risk scores of the population sharing one or more attributes with the user profile. Furthermore, the front-end visualization engine may display different input values within a factor or subset of inputs. The front end visualization engine may enable a hierarchical display such that an enterprise user can seamlessly transition between information at differing levels of abstraction.

In an embodiment, a computer implemented method comprises displaying, by a computer, a first level display with at least a subset of a filtered list of a plurality of users and a plurality of filtering graphical elements allowing a dynamic update to the filtered list of the plurality of users; in response to the computer receiving a selection of a first user: displaying by the computer, a second level display wherein the second level display contains: a user identification graphical element containing one or more pieces of information identifying the first user and one or more attributes of the first user; a risk class graphical element displaying the risk class of the first user; a risk score graphical element displaying the risk score of the first user; a model graphical element displaying an identification of a machine learning model used to generate the risk score of the first user; a first color coded histogram showing a distribution of risk score of the plurality of users, wherein the risk score of the first user is juxtaposed in the first color coded histogram; a second color coded histogram showing a percentile distribution of the plurality of users, wherein the percentile position of the first user is juxtaposed on the second color coded histogram; a first set of horizontal bars in a first color stretching in a first direction from a zero-line, wherein each horizontal bar in the first set of horizontal bars indicates a respective negative factor negatively contributing to the risk score and the length of the horizontal bar indicates the magnitude of the negative contribution of the respective negative factor; a second set of horizontal bars in a second color stretching in a second direction from a zero-line, wherein each horizontal bar in the second set of horizontal bars indicates a respective positive factor positively contributing to the risk score and the length of the horizontal bar indicates the magnitude of the positive contribution of the respective positive factor; and in response to the computer receiving a selection of a horizontal bar in the first and second set of horizontal bars: dynamically updating, by the computer, the second level display to display an input value within a factor indicated by the selected horizontal bar, wherein the input value is juxtaposed within a box plot of the corresponding input values received from the plurality of users.

In another embodiment, a system comprises a non-transitory storage medium storing a plurality of computer program instructions; and a processor electrically coupled to the non-transitory storage medium and configured to execute the plurality of computer program instructions to: display a first level display with at least a subset of a filtered list of a plurality of users and a plurality of filtering graphical elements allowing a dynamic update to the filtered list of the plurality of users; in response to the processor receiving a selection of a first user: display a second level display wherein the second level display contains: a user identification graphical element containing one or more pieces of information identifying the first user and one or more attributes of the first user; a risk class graphical element displaying the risk class of the first user; a risk score graphical element displaying the risk score of the first user; a model graphical element displaying an identification of a machine learning model used to generate the risk score of the first user; a first color coded histogram showing a distribution of risk score of the plurality of users, wherein the risk score of the first user is juxtaposed in the first color coded histogram; a second color coded histogram showing a percentile distribution of the plurality of users, wherein the percentile position of the first user is juxtaposed on the second color coded histogram; a first set of horizontal bars in a first color stretching in a first direction from a zero-line, wherein each horizontal bar in the first set of horizontal bars indicates a respective negative factor negatively contributing to the risk score and the length of the horizontal bar indicates the magnitude of the negative contribution of the respective negative factor; a second set of horizontal bars in a second color stretching in a second direction from a zero-line, wherein each horizontal bar in the second set of horizontal bars indicates a respective positive factor positively contributing to the risk score and the length of the horizontal bar indicates the magnitude of the positive contribution of the respective positive factor; and in response to the processor receiving a selection of a horizontal bar in the first and second set of horizontal bars: dynamically update the second level display to display an input value within a factor indicated by the selected horizontal bar, wherein the input value is juxtaposed within a box plot of the corresponding input values received from the plurality of users.

BRIEF DESCRIPTION OF THE DRAWINGS

The accompanying drawings constitute a part of this specification and illustrate embodiments of the subject matter disclosed herein.

DETAILED DESCRIPTION

Figure 1:
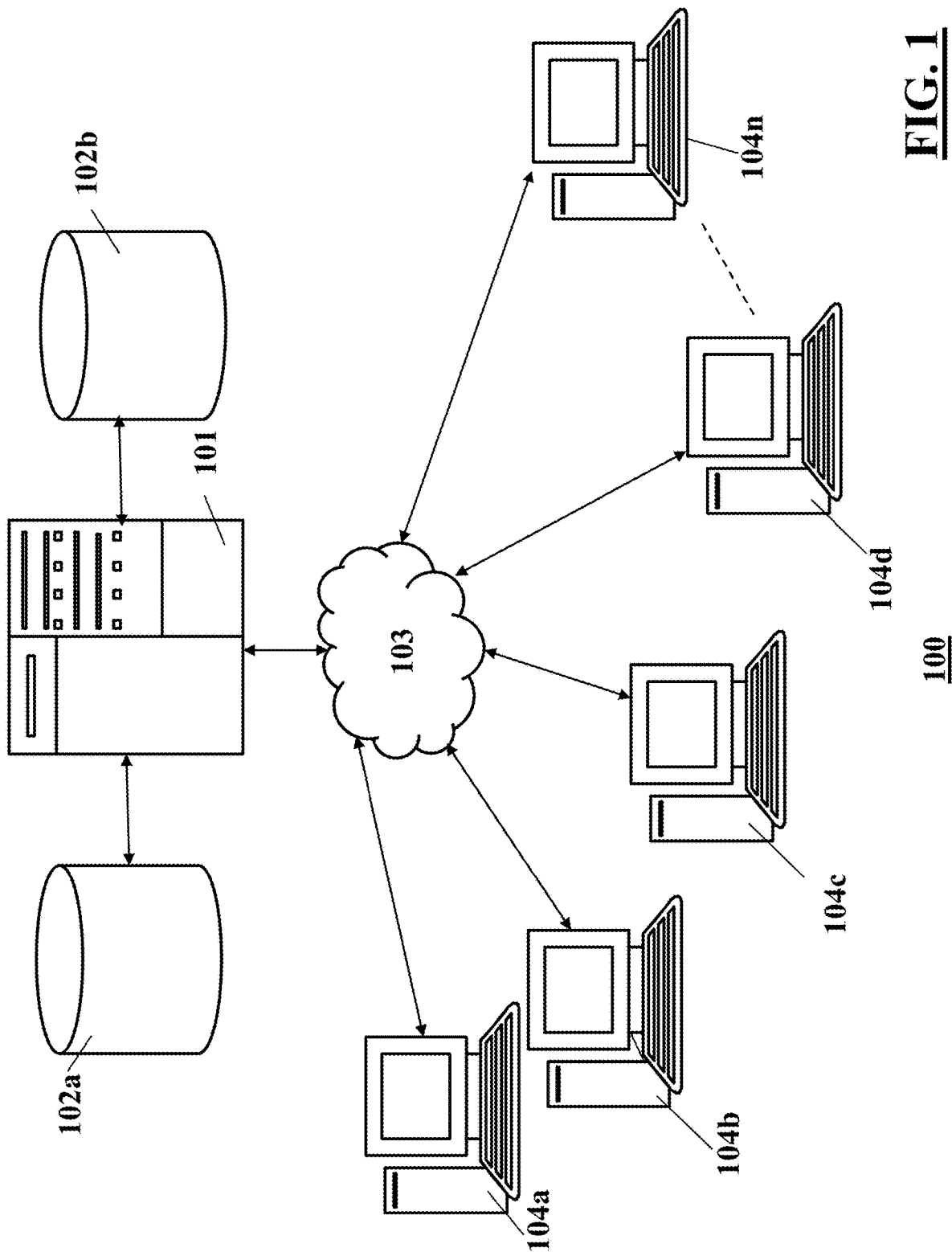
FIG. 1 shows an exemplary system, according to an exemplary embodiment.

Reference will now be made to the illustrative embodiments illustrated in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Embodiments disclosed herein provide a back-end computer infrastructure and a front-end visualization engine to generate a risk score and contributing factors for a user profile of a general user and display the risk score to enterprise users. As used herein, a "general user" or simply a "user" may refer to a user whose profile has to be scored and "enterprise user" may refer to a user employed by the company that maintains the back-end computer infrastructure. A computer within the back-end computer infrastructure train one or more machine learning models to score general user profile. The machine learning models may be different for different sets of general users having different attributes. For example, the computer may use a first machine learning model to score user profiles of general users within the age range of thirty-five to forty and a second machine learning model to score user profiles of general users within the age range of forty to forty five. To train a machine learning model, the computer may use a set of inputs and known outputs corresponding to the set of inputs. The computer may train the machine learning model to ascertain the statistical dependencies among different factors. For example, there may be a statistical dependence between weight and blood pressure, and the machine learning model may take into account the interaction between these variables to compute the risk score. These interactions may be quite subtle and may require a machine learning model to weigh each of these factors to generate a risk score.

The back-end computer infrastructure may generate different baseline reference profiles for different sets of general users having different attributes. For example, a baseline reference profile for tobacco users may be different from a baseline reference profile for users who do not use tobacco. The computer may include median input values (also referred to as attributes) of the respective set of general users to a baseline reference profile. The computer may group the input values into different groups, or factors. For example, a blood pressure factor may include input values of diastolic blood pressure, systolic blood pressure, and standard pulse at rest.

The computer may receive a plurality of input values associated with a first user. From the plurality of input values, the computer may generate a user profile for the first user by grouping the input values into different factors. The computer may then use a respective machine learning model to score the user profile. To do so, the computer may retrieve a respective baseline reference profile based on the user profile. The computer may perturb the different input values within the baseline profile in stepwise fashion until the user profile is reached. The computer may generate an intermediate risk score for each perturbation and generate a final risk score once all stepwise perturbations are complete.

A front-end visualization engine may present a hierarchical and interactive display showing various pieces of information associated with the user profile and the calculated risk scores. At a first level of hierarchy, the front-end visualization engine may display a filtered list of general users and provide various graphical filtering tools to further filter the list of general users. An enterprise user may interact with an entry of a general user in the filtered list and the visualization engine may present a second display at a second level of hierarchy. The second display may present the final risk score the user juxtaposed within the risk score distribution of a population of general users having one or more attributes as the user. The second display may also graphically present various factors contributing to the risk score. When the enterprise user interacts with a graphical display of a factor, the visualization engine may present the input values within the factor for the user juxtaposed with the input values of the aforementioned population of the general users. The visualization engine may allow the enterprise user to seamlessly transition between the displays of different hierarchies.

FIG. 1 shows an exemplary system 100, according to an exemplary embodiment. The exemplary system 100 may comprise one or more servers 101, one or more databases 102, a communication medium 103, and one or more workstation terminals 104. One having ordinary skill in the art appreciates that the system 100 is not confined to the components described herein and may comprise additional or alternate components, which are to be considered within the scope of the exemplary embodiment. Furthermore, functionality attributed to a component of the exemplary system 100 may be fully or partially executed by other components of the system 100.

The servers 101 of the exemplary system 100 may execute various software modules that instruct the servers 101 on performing one or more processes for receiving data from various devices, storing the received data in the databases 102, retrieving data stored in databases 102, and performing various operations on the retrieved data. A server 101 may be any computing device comprising non-transitory machine-readable storage media and a processor capable of executing the various processes and tasks described herein. Non-limiting examples of a server 101 may include a server computer, a desktop, a laptop, a tablet, or the like. In some cases, the server 101 may be coupled to the databases 102 of the system 100, and, in some cases, the server 101 may host the one or more databases 102.

In some embodiments, a server 101 may host an application server or webserver, either of which may include software modules allowing the workstation terminals 104 to access and/or manipulate data in a database 102 or in the server 101. For example, the server 101 may comprise a webserver allowing the workstation terminals 104 to access data that is collected and manipulated by the server 101. In this example, an agent associated with the system 100, who may be operating a workstation terminal 104, may point a web browser application executed by the workstation terminal 104 to a website hosted on the webserver in order to access the data stored in the database 102 and results generated by the server 101. In another example in which the server 102 comprises a web-accessible application server, a terminal workstation 104 may be a mobile device (e.g., tablet, laptop, smart phone) executing a software application configured to access the system 100. In this example, an agent associated with the system 100 may use the mobile application to interact with the server 101 and the databases 102.

The databases 102 may contain user profiles of a plurality of users. Each user profile may be a data record with multiple fields storing pieces of information of the respective user. The multiple fields may include, for example, age, gender, smoking habit, drinking habit, laboratory values, family history, and/or types of fields collecting data from the user. The server 101 may implement one or more machine learning algorithms to score the user profiles stored in the databases 102. To do so, the server 101 may train a machine learning model using known inputs and known outputs. The server 101 may store the machine learning model in the databases 102 and may use the machine learning model as an inferential engine to score the user profiles. The server 101 may also implement a visualization engine to display the results of computing the risk scores for one or more users using one or more machine learning models. The visualization engine may display graphic elements such as bar graphs, charts, and stepwise charts such that the scoring process remains transparent from the perspective of an enterprise user using a terminal workstation 104.

The communication medium 103 may be any type of communication medium such as a local area network (LAN), metropolitan area network (MAN), and/or a wide area network (WAN). For instance, the communication medium 103 may be the internet. The communication medium 103 may be a combination of various wired and wireless links capable of carrying data packets in between the server 101 and the workstation terminals 104.

The workstation terminals 104 may be any type of computing devices used by agents associated with the system 100. Non limiting examples of workstation terminals 104 may be a laptop computer, a desktop computer, a smart phone, and a tablet computer. The workstation terminals 104 may have a software application allowing a user to access the server 101 through the communication medium 103. In addition or in the alternative, a user may access the server 101 through a web-browser running on the workstation terminals 104.

Figure 2:
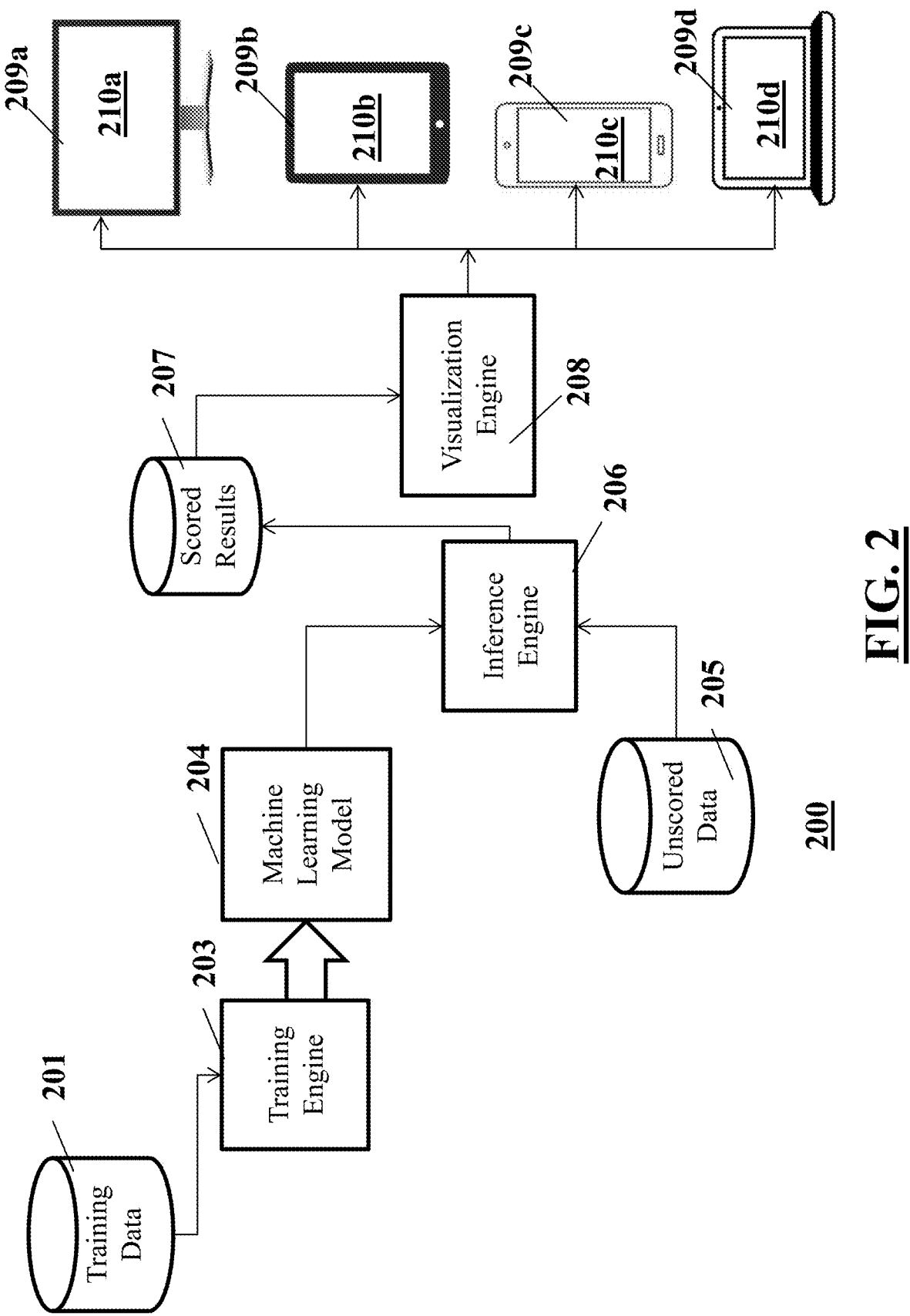
FIG. 2 shows an exemplary machine learning system, according to an exemplary embodiment.

FIG. 2 shows an exemplary system 200, according to an exemplary embodiment. The components shown in FIG. 2 and described herein are merely exemplary and components may be added, subtracted, or substituted without deviating from the scope of this disclosure. A set of training data 201 may include known inputs and the corresponding known outputs to train the machine learning model 204. A training engine 203 may include hardware and software modules to train the machine learning model 204 using the set of training data 201. The hardware and software modules may include one or more processors and the respective instructions sets to feed in the known inputs and the corresponding known outputs into the training engine 203. The machine learning model 204 may include hardware and software modules containing weights for a plurality of variables for the inputs in the set of training data 201. The training model 203 may feed the known inputs and the corresponding known outputs to the machine learning model 204 such that the machine learning model 204 may iteratively modify the weights for the input variables to generate the corresponding known outputs. As mentioned above, the machine learning model 204 may have the iteratively generated and finalized weights for the known input variables to generate the corresponding known outputs. The inference engine 206 may take in the machine learning model 204 unscored data 205 as inputs to generate the scored results 207. The scored results 207 may then be displayed in the graphical user interfaces (GUIs) 210 of the terminal devices 209 using the visualization engine 208.

Figure 3:
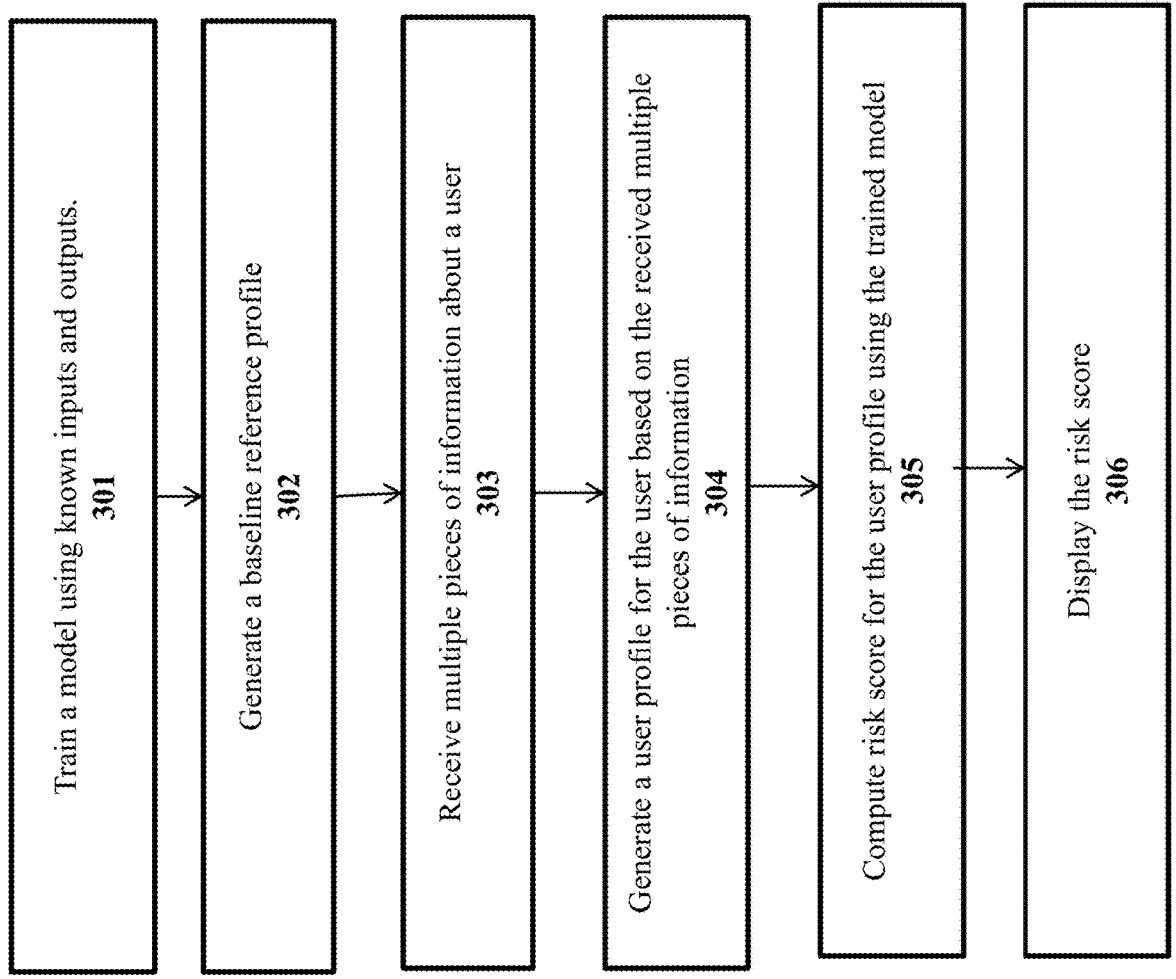
FIG. 3 shows an exemplary method, according to an exemplary embodiment.

FIG. 3 shows an exemplary method 300 of computing risk scoring, according to an exemplary embodiment. Although one or more computers and associated databases may perform one or more steps of the method 300, this description details, for brevity, a computer implementing the method 300. It should be understood that the following steps are merely exemplary, and the method 300 may have additional or alternative steps or may skip one or more steps altogether.

In step 301, the computer may train a model using known inputs and outputs contained in a training dataset. Algorithms and their implementations leverage training data to learn the structure and parameters of machine learning and statistical models via objective functions that connect inputs to their corresponding outputs. The objective functions generally aim to optimize the error associated with estimates of the outputs solely using the inputs and the actual known outputs. In some embodiments, the machine learning model may be a tree structured model, which may subdivide a population based on different factors and repeatedly iterate through the population on determine the signals for each of the different factors.

For example, in the context of mortality risk scoring, the computer may collect multi-year dataset from a plurality of users. The multi-year dataset may include various medical and health data (e.g., cholesterol readings, weight), occupation data (e.g., type of day job), substance usage data (e.g., smoker vs. non-smoker), and/or any other type of data. The dataset may also contain mortality data, e.g., the age and circumstances of corresponding user's death. The computer may use this dataset to train the machine learning model. For example, the computer may use a dataset collected every six months to train the machine learning model. In other examples, the computer may use a dataset collected every quarter to train the machine learning model.

In some embodiments, the computer may use a cost regression model as the machine learning model. Using the cost regression model, the computer may fit input variables (e.g., the medical and health data) into a response variable that describes a survival time (e.g., number of years a user is expected to live). For the fitting, the computer may use least squares to quantify the error and iteratively train the model until the desired level of error is reached. In some embodiments, the computer may use a random survival forest model (e.g., a collection of decision trees, where a number of trees and a depth of trees is compared and optimized as data changes/updated) as the machine learning model. For each of the trees within the random survival forest model, the computer may choose an input that maximizes a particular test statistic. For example, the computer may choose age as an input and split users into two groups, one group that has age less than a threshold age and another group that has age more than the threshold age. The computer may choose the age such that the survival characteristic of these two groups, i.e., the difference between the two groups, is maximized. The computer may quantify the difference through long-range statistics that is computer via comparing a Kaplan-Meier estimator between survival curves of the two groups. It should be understood that these models are merely exemplary and other models should also be considered within the scope of this disclosure. Furthermore, the computer may utilize a combination of models, e.g., a combination of the cost regression model and the random survival forest model, as the machine learning model.

In step 302, the computer may generate a baseline reference profile for the general users. In some embodiments, the computer may generate a baseline reference profile for each cohort of general users. For example, the computer may generate a first baseline reference profile for a population of general users who are female non-smokers between the ages of thirty and thirty five. The computer may generate a second baseline reference profile for a population of general users who are female smokers between the ages of thirty and thirty five. Each of the baseline profiles may include median values for different attributes within the cohort. For example, in the first baseline reference may contain median values of labs such as cholesterol, blood pressure, pulse, which collectively indicate that a general user with attributes within the first baseline reference may generally be very healthy. It should be understood that the baseline reference profile may be embedded within the machine learning model. In other words, the machine learning model may learn the baseline profile through the iterative trainings.

In step 303, the computer may receive multiple pieces of information about a user. The computer may receive the multiple pieces of information from a workstation terminal. In some instances, an agent at the workstation terminal may use a web browser to access an interface generated by the computer. The interface may contain various graphical tools for the agent to enter the multiple pieces of information. The graphical tools may include, for example, electronic forms, dialog boxes, popup boxes, radio buttons, and/or any other graphical tools. In other instances, the agent the workstation may use a standalone application running on the workstation computer. The standalone application may communicate with the computer and receive instructions from the computer to generate an interface for the agent to enter the multiple pieces of information. As in the web browser environment, the interface displayed by the standalone application may include graphical tools such as electronic forms, dialog boxes, popup boxes, radio buttons, and/or any other graphical tools for the agent to enter the one or more pieces of information. Furthermore, the computer may receive the multiple pieces of information from other sources such as tablets, smartphones, and/or any other type of computing devices. The computer may instruct a web-browser or any other standalone application running on these computing devices to display an interface such that an agent or another user may enter the multiple pieces of information.

The computer may retrieve the multiple pieces of information from one or more databases. In some instances, the computer may directly retrieve data records with the pieces of information using a direct query to the one or more databases. In other instances, the computer may use an application programming interface (API) associated with the one or more databases to send a request for and receive the pieces of information.

The multiple pieces of information may include pieces of information about a user. The pieces of information may include demographic information such as age and gender. The pieces of information may also include, for example, lifestyle information indicating whether the user is a smoker or a non-smoker. Other lifestyle information may include the drinking habits of the user such as quantified consumption of alcoholic beverages, for example, glasses of wine per day. Lifestyle information may also include exercise habits, such as the number of hours spent per week in the gym. In some implementations, the computer may retrieve the lifestyle information from smart devices such as smartwatches or exercise tracker applications installed in smartphones, using the respective API's. The pieces of information may also include family history information, such as the presence or absence of hereditary and genetic diseases such as diabetes, cancer, and heart disease in the family. Furthermore, the pieces of information may include laboratory values for the user. The laboratory values may include, for example, blood sugar levels, cholesterol levels, liver enzyme levels, other lipid levels, and/or other types of laboratory values collected at one or more times.

In step 304, the computer may generate a user profile from the user based upon the multiple pieces of information. The multiple pieces of information may describe the attributes (or input values) associated with the user. For example, a first piece of information may indicate the age of the user, a second piece of information may indicate the gender of the user, and a third piece of information may indicate blood cholesterol level of the user. The computer may insert the multiple pieces of information into various fields of the data record defining the user profile of the user. The computer may group the input values into different factors.

In step 305, the computer may compute risk score for the user profile using the machine learning model. The computer may first retrieve a baseline reference profile for the cohort the general user belongs to. For example, the if the general user is a female non-smoker aged thirty one, the computer may retrieve a baseline reference profile for a population of female non-smokers between the age of thirty and thirty five.

The machine learning model may step through each input value (or attribute) in the user profile using a respective weight for the input value. More specifically, the machine learning model may start from the baseline reference profile, which, as one can appreciate, may have a very low risk score. The machine learning model may then in a stepwise fashion perturb the input values within the different factors in the baseline reference model with the values in the user profile until the model reaches the user profile. Within each step of the process, the machine learning model may generate an intermediate risk score based on a preceding perturbed value. In other words, the model may rescore the baseline reference model for each perturbation for each of the perturbing values in the user profile. The model may step through the factors (and the underlying values) until the model reaches the user profile to generate a final risk score. The aforementioned scoring process using the machine learning model may be model-agnostic because each step of rescoring a perturbed baseline reference profile until the computer reaches the user profile is not dependent upon the underlying machine learning model. In other words, the computer may use any type of underlying model for the stepwise perturbation and score recalculation.

Furthermore, a machine learning model may take into multiple entangled variables during the step-wise risk calculation. For example, a general user may have high cholesterol thereby placing the general user to a higher risk class. However, if the machine learning model may determine the fact that the general user is taking a prescription medication to lower the high cholesterol, the machine learning model may lower the risk class based on the fact the general user is taking remedial measures for lowering a risk factor. Furthermore, as the process is transparent to the enterprise as the enterprise user may see the factors contributing to risk score, the enterprise user may offer additional advice to the general user for lowering the risk class. To that end, when a general user does not qualify, the computer may automatically send a notification to the enterprise user instructing the enterprise user to initiate a communication with the general user on lowering the risk score by working on one or more factors that contributed to a higher risk score. The machine learning model may also integrate related factors. For example, the machine learning model may not change the risk score when a body mass index (BMI) is entered in lieu of height and weight of a general user.

In step 306, the computer may display the risk score. In addition to the composite risk score, the computer may display all the steps undertaken to reach to the composite score. The computer system may display the steps as a graph such as a line graph or a bar graph.

Figure 4:
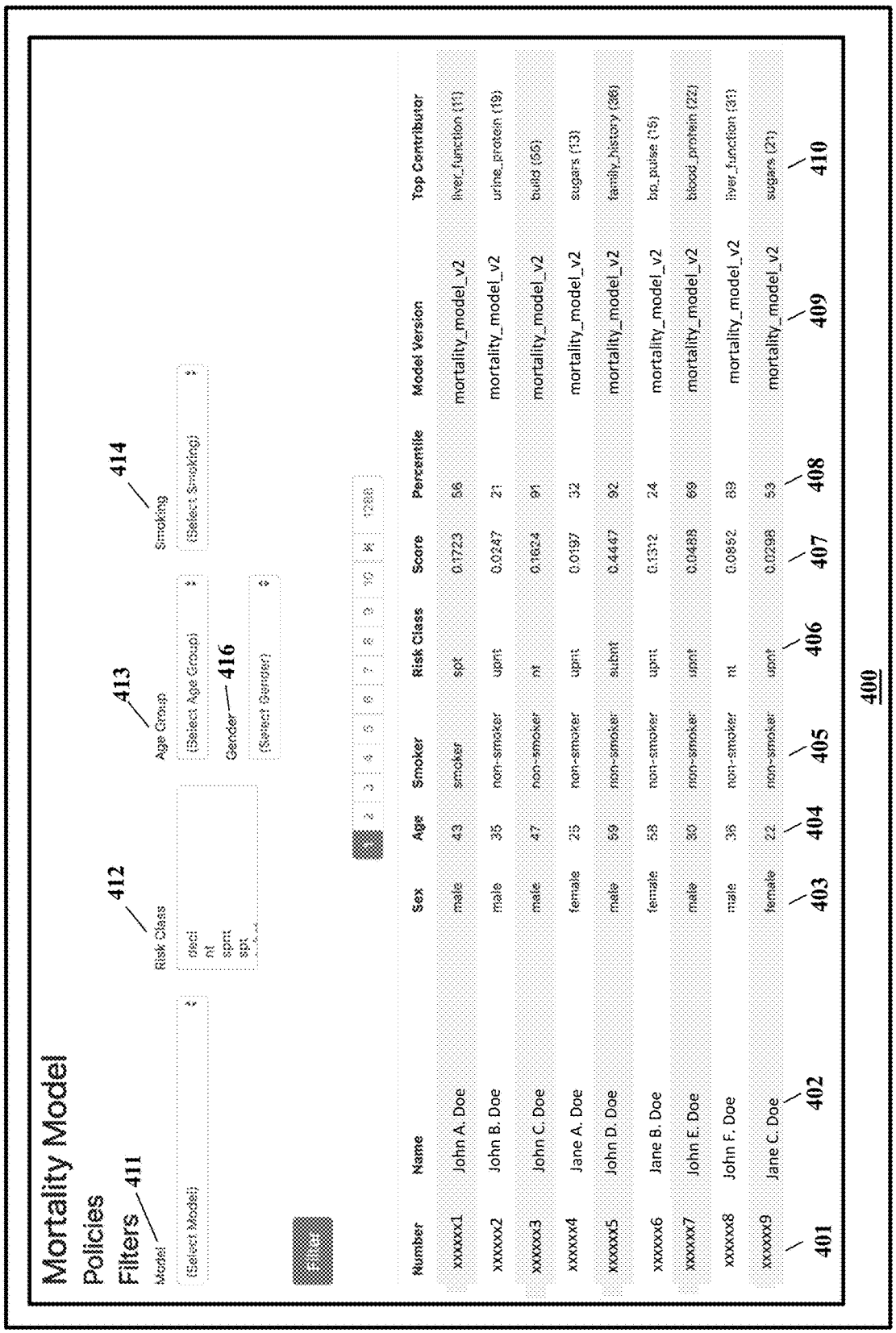
FIG. 4 shows a first exemplary graphical user interface (GUI), according to an exemplary embodiment.

FIG. 4 shows an exemplary graphical user interface (GUI) 400, according to an exemplary embodiment. As shown, the exemplary GUI 400 may show a paginated view of general users registered to a system. The paginated view may allow an enterprise user to interact with one or more filtering graphic elements (such as selection and dropdown menus) 411, 412, 413, 414 to apply one or more filters to the paginated view. The filtering graphic elements 411, 412, 413, 414 may allow the system to compare the general users within their cohorts having similar attributes.

The exemplary GUI 400 may display a filtered listing of general users in a table. The exemplary GUI 400 may enable an enterprise user to filter and display general users based one or more filters. The model filter dropdown menu 411 may allow the enterprise user to filter the listing of general users based on machine learning models used to score the general users' respective user profiles. The risk class selection menu 412 allows the enterprise user to select the risk to apply the selected risk class to be applied as a filter while displaying the filtered listing of the general users. The age group dropdown menu 413 may allow the enterprise user to filter using the age group while displaying the filtered listing of the general users. The age group dropdown menu 413 may allow an enterprise user to filter the listing based upon age ranges such five years or ten years. The smoking dropdown menu 414 allows the enterprise user to filter the listing of the general users based on the smoking status of the general users. The smoking status may indicate that the corresponding general user is a smoker or a non-smoker.

The filtered listing of general users may comprise a table with plurality of columns: for example, number 401, name 402, sex 403, age 404, smoker status 405, risk class 406, risk score 407, percentile 408, model version 408, and top contributor 410. The number column 401 may indicate the respective registration numbers for the general users listed in the table. The back-end computer infrastructure may have provided the register number to the general users as a part of the registration process. The name column 402 may indicate the respective names of general users. The sex column 403 may indicate the respective genders of the general users. As shown, the sex column 403 may indicate whether the respective general user is a male or a female. The age column 404 may show the respective ages of the general users. The smoker column 405 may indicate the respective smoking statuses of the general users. For example, the smoker column 405 may indicate whether the respective general user is a "smoker" or a "non-smoker." The risk class column 406 may indicate the respective risk classes of the general users.

The score column 407 may indicate the respective risk scores of the general users. The percentile column 408 may indicate the respective risk percentiles of the general users. The model version column 409 may indicate the respective model versions to score the user profiles of the general users. The top contributor column 410 may indicate the respective top contributors for the risk scores for the general users.

In the paginated view displayed by the GUI 400, the computer may allow the enterprise user to click on the data record for an individual general user. For example, the enterprise user may click on a specific policy number in the number column 401. Once the enterprise user clicks on a specific policy number in the number column 401, the computer may display the exemplary GUI 500 as shown in FIG. 5.

Figure 5:
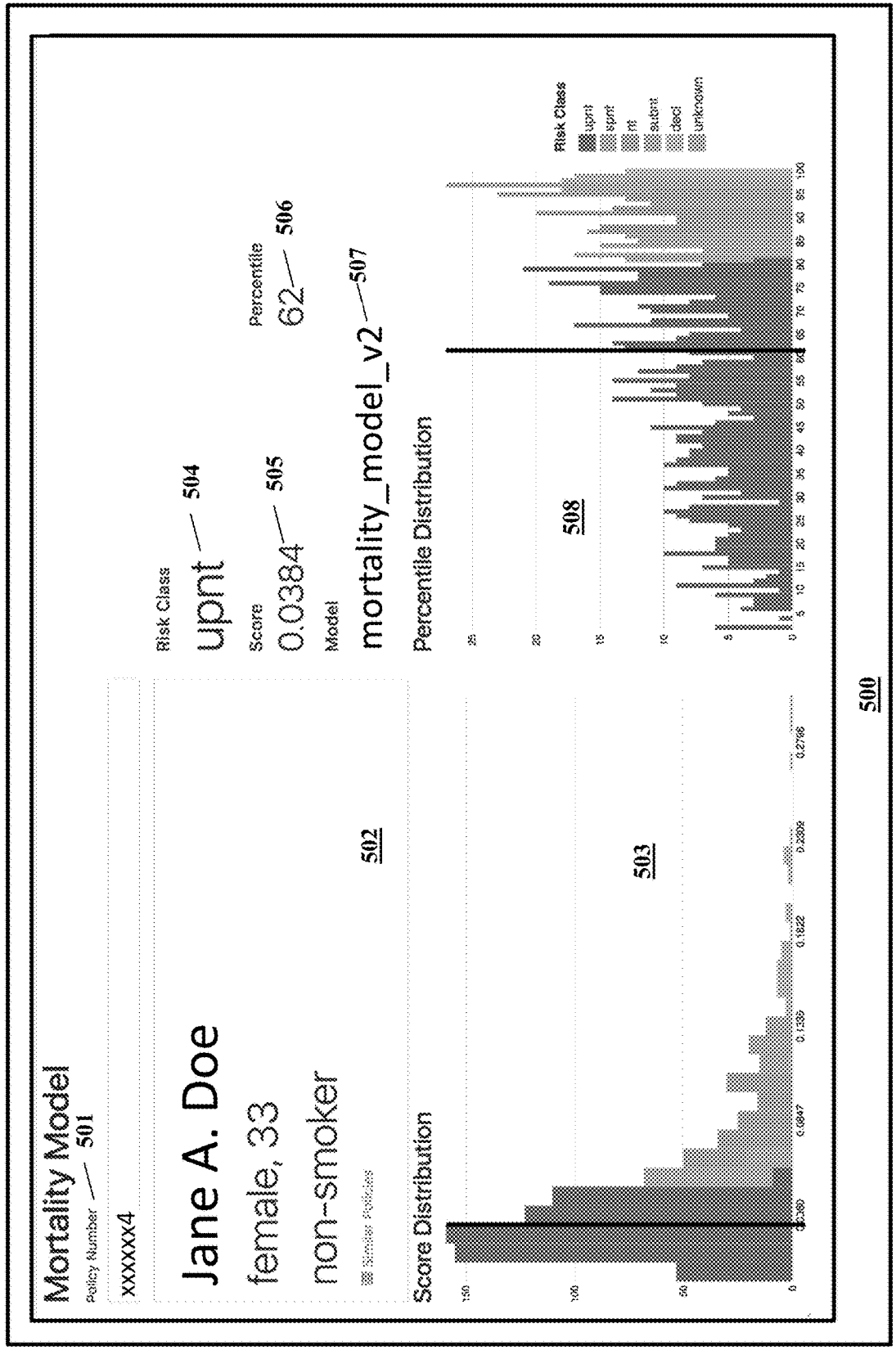
FIG. 5 shows a second exemplary GUI, according to an exemplary embodiment.

FIG. 5 shows the exemplary graphical user interface (GUI) 500, according to an exemplary embodiment. The exemplary GUI 500 may display risk profile for an individual general user. As described above, the computer may display the risk profile on the individual user whose policy number may have been clicked in the exemplary GUI 400 by an enterprise user.

The policy number graphic element 501 may display the policy number of the general user. The identification graphic element 502 may display identification information of the general user. As shown herein, the identification information displayed by the identification graphic element 502 may include name of the, gender, age, and smoking status of the general user. The score distribution graphic element 503 may display score distribution for a plurality of general users alongside the score of the general user. More specifically, the score distribution graphic element 503 may display a score distribution histogram indicating the score distribution of the population and may juxtapose the score of the general user in the score distribution histogram. In the score distribution histogram, the X-axis may represent a plurality of score ranges (shown as bins in the score distribution histogram) and Y-axis may represent the number of general users in the population for each score range. The score distribution graphic element 503 may allow for the enterprise user to change the range of values represented by each bin. Furthermore, the score distribution graphic element 503 may allow the enterprise user to define the number bins in the score distribution histogram.

The percentile distribution graphic element 508 may display score distribution for a population of general users alongside the score of the general user identified in the identification graphic element 502. More specifically, the percentile distribution graphic element 508 may display a percentile distribution histogram indicating the percentile distribution of the population and may juxtapose the percentile position of the general user in the percentile distribution histogram. In the percentile distribution histogram, the X-axis may represent the percentile and Y-axis may represent the number of general users in the population for each percentile. The percentile distribution graphic element 508 may allow for the enterprise user to change the scale of one or more of the X-axis and the Y-axis. Furthermore, the percentile distribution graphic element 508 may allow the enterprise user to define one or more bins as percentile ranges in the percentile distribution histogram.

The computer, in the GUI 500, may color code each of the distribution histograms in the score distribution graphic element 503 and percentile distribution graphic element 508. The color code may be based upon the risk class of the general users in the population. For example, in the percentile distribution graphic element 508, the general users below the eightieth percentile may be deemed within an ultra-preferred risk class non-tobacco (upnt) and the computer may user a first color to color the segment of the percentile distribution histogram until the eightieth percentile. Between the eightieth and ninetieth percentile, the risk class may be standard-preferred non-tobacco (spnt), and the computer may use a second color to indicate upnt risk class. Between nineteenth and ninety sixth percentile, the risk class may be non-tobacco (nt), and the computer may use third color to indicate the nt risk class. Between ninety sixth and ninety ninth percentile, the risk class may be substandard non-tobacco (subnt) and the computer may color code this risk class using a fourth color. Beyond ninety ninth percentile, the risk class may be declined (decl) and the computer may use a fifth color to color code this risk class. Furthermore, the computer may color code the score distribution histogram in the score distribution graphic element 503. The risk score in the score distribution histogram may correspond to the percentiles in percentile distribution histogram and the computer may color code the score distribution histogram accordingly. In some embodiments, the computer may use the same colors from the percentile distribution histogram to color code the corresponding distributions score distribution histogram. In other embodiments, the computer may use different colors from the percentile distribution histogram in the score distribution histogram. Regardless of the coloring scheme, the score distribution histogram may use threshold score values to classify the general user population to different risk categories and use a color for each of the risk categories. Therefore each of the score distribution graphic element 503 and the percentile distribution graphic element 508 allow the enterprise user to observer the risk position of a general user compared to the distribution of risk in the general population.

The computer may select a population of general users based upon one or more attributes of a user. For example, the computer may select a group of general users who female non-smokers and within the age range of 30-40 years. More specifically, the machine learning model being implemented by the computer may automatically select a segment of the total population, wherein the people within the segment share one or more attributes.

Figure 6:
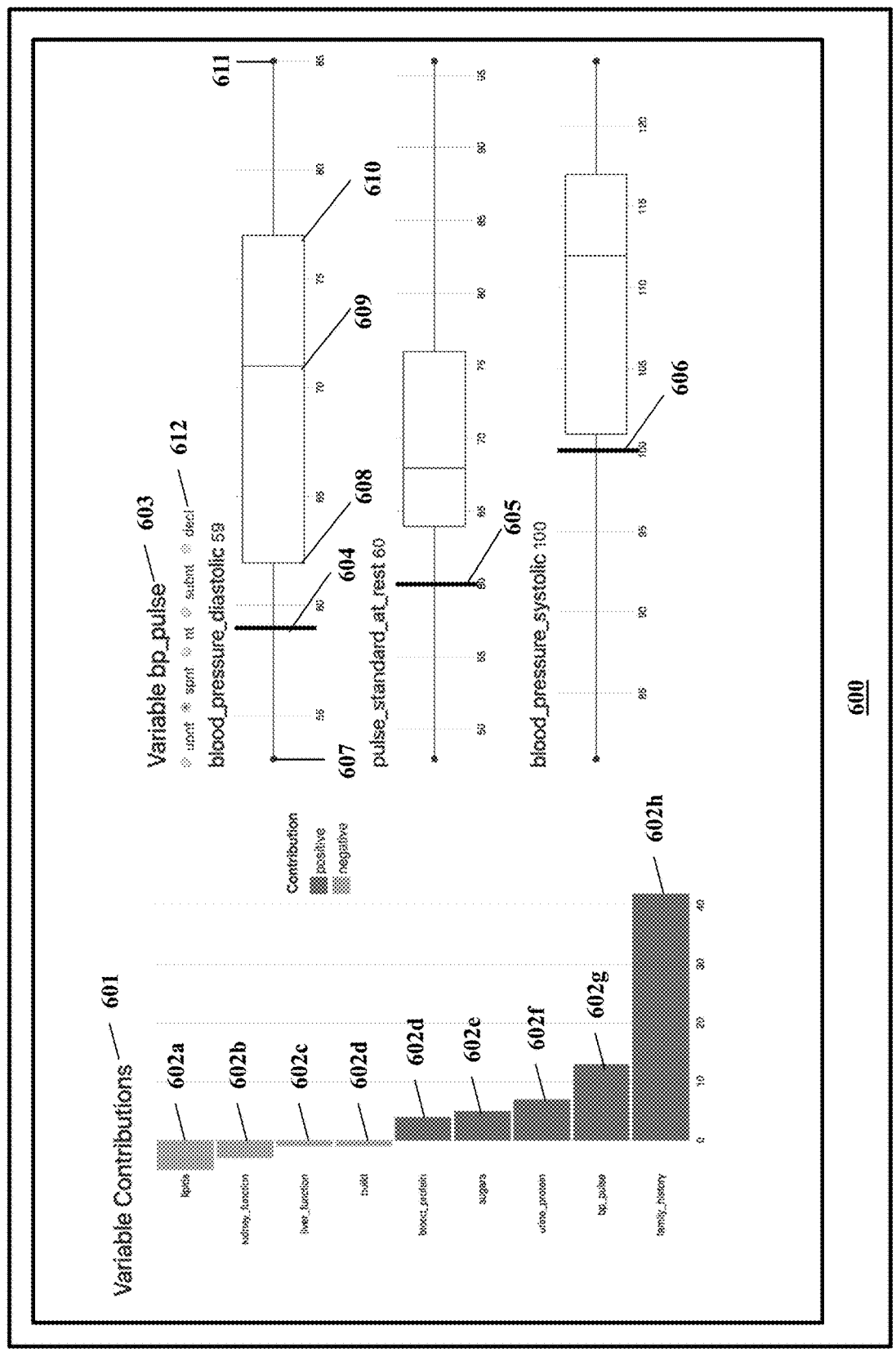
FIG. 6 shows a third exemplary GUI, according to an exemplary embodiment.

FIG. 6 shows an exemplary graphical user interface (GUI) 600, according to an exemplary embodiment. The GUI 600 may display the contributing factors to the risk score in a logical and an ordered fashion. The variable contributions graphic element 601 may display graphical representations 602 of the plurality of contributing factors for a general user. As shown herein, the variable contribution graphic element 602 may display a horizontal bar graph with the factors with positive contribution to the right of the zero-line in the middle and factors with negative contribution to the left of the zero-line. More specifically, factors 602a, 602b, 602c, 602d may be factors with negative contributions to the risk score and factors 602d, 602e, 602f, 602g, 602h may be factors with positive contributions to the risk score. The length of each of the factors 602 may represent the degree of contribution—positive or negative—of the respective factor 602. Therefore, an enterprise user may readily see the relative contribution of each factor 602 in the GUI 600. At the back-end, a machine learning model may calculate the length of each of the factors 602. In some implementations, the a computer displaying the GUI 600 may display the most important contributing factors in a different color scheme than relatively less significant factors.

Within the GUI 600, each of the factors 602 are clickable by the enterprise user. When a factor 602 is clicked upon, the computer may load input values of the general user. More specifically, the computer may load the inputs that are grouped within a factor by the machine learning model. In other words, each of the factors 602 may represent a category that can be broken down into actual inputs entered by the general user.

The individual factor detailed display graphical element 603 may graphically display the inputs 604, 605, 606 within the individual factor. As, shown herein, the individual factor detail display graphical element 603 may display be bp_pulse ("blood pressure and pulse"), and the input may be blood_pressure_diastolic 604, pulse standard at rest 605, and blood_pressure_systolic 606. As shown herein, the computer may juxtapose each of the inputs 604, 605, 606 as a straight line within a box plot displaying the range of the rest of the population with one or more attributes similar to the general user. A box plot, as shown herein may display five metrics of a numeric variable having a range of values: the minimum, the maximum, the twenty fifth percentile, the fiftieth percentile (median), and the seventy-fifth percentile. As an example, for the input blood_pressure_diastolic 604, the minimum is indicated as 607, the twenty-fifth percentile as 608, the median as 609, the seventy fifth percentile as 610, and the maximum as 611. As mentioned above, the actual input of the general user for blood_pressure_diastolic is shown as 604.

The GUI 600 may also display box plots (or any other type of display element) for the different risk class based on the enterprise user's selection of the radio buttons 612. In doing so, the computer may juxtapose the input of the general user in the distribution of the population in a different risk class. Such cross-comparison may allow the enterprise user to suggest how the general user may improve his risk class. For example, the enterprise user may juxtapose the input of the general user to a lower risk class, which may have to pay a lower premium than the risk class the general person is in. Based the juxtaposition, the computer may allow the enterprise user to advice the general user how the risk class can be improved. For example, a general user may be below a twenty fifth percentile of a first risk class that is higher than a second risk class. The enterprise user may click on one of the radio buttons 612 to ascertain where the general user falls in the second risk class. If the general user falls in above the seventy fifth percentile of the second risk class, the enterpriser user may advice the status to the general user and further advice the general user that his risk class can be lowered by working on the particular input, for example, lowering the blood pressure to lower than the twenty fifth percentile of the second risk class.

The GUI 600 may also include a link or any other type of graphical element (not shown) that allows an enterprise user to list general users similar to the general user referenced herein. When the enterprise clicks on the link or otherwise interact with the graphical element, the computer may automatically filter the general users based on the attributes of the general user referenced herein. For example, the computer may retrieve the list of general users who have the same age range, same smoking habits, and same machine learning model as the general user referenced herein. This allows the enterprise user to see if other general users with similar attributes as the general user referenced herein got a better policy compared to the general user referenced herein.

The exemplary GUIs 400, 500, 600 are described as being used by an enterprise user for the sake of brevity. However, the exemplary GUIS 400, 500, 600 may be consumer facing as well, that is, the computer may allow the general users to access and interact with the exemplary GUIs 400, 500, 600. Other illustrative consumer facing GUIs are described below in reference to FIGS. 8A-8O. The computer may receive various inputs from the general users and dynamically update one or more of the exemplary GUIs 400, 500, 600 based on the received inputs. A general user may then be able to see the change in risk scores based upon the inputs. In other words, the computer may aid the general user to understand if they can improve upon one or more inputs to improve their respective risk scores. In yet another words, the computer may provide, through the exemplary GUIs 400, 500, 600, a flexible calculator type environment, wherein the general users may enter their known inputs and toggle through the known inputs to see how the toggling effect their risk scores.

Figure 7A:
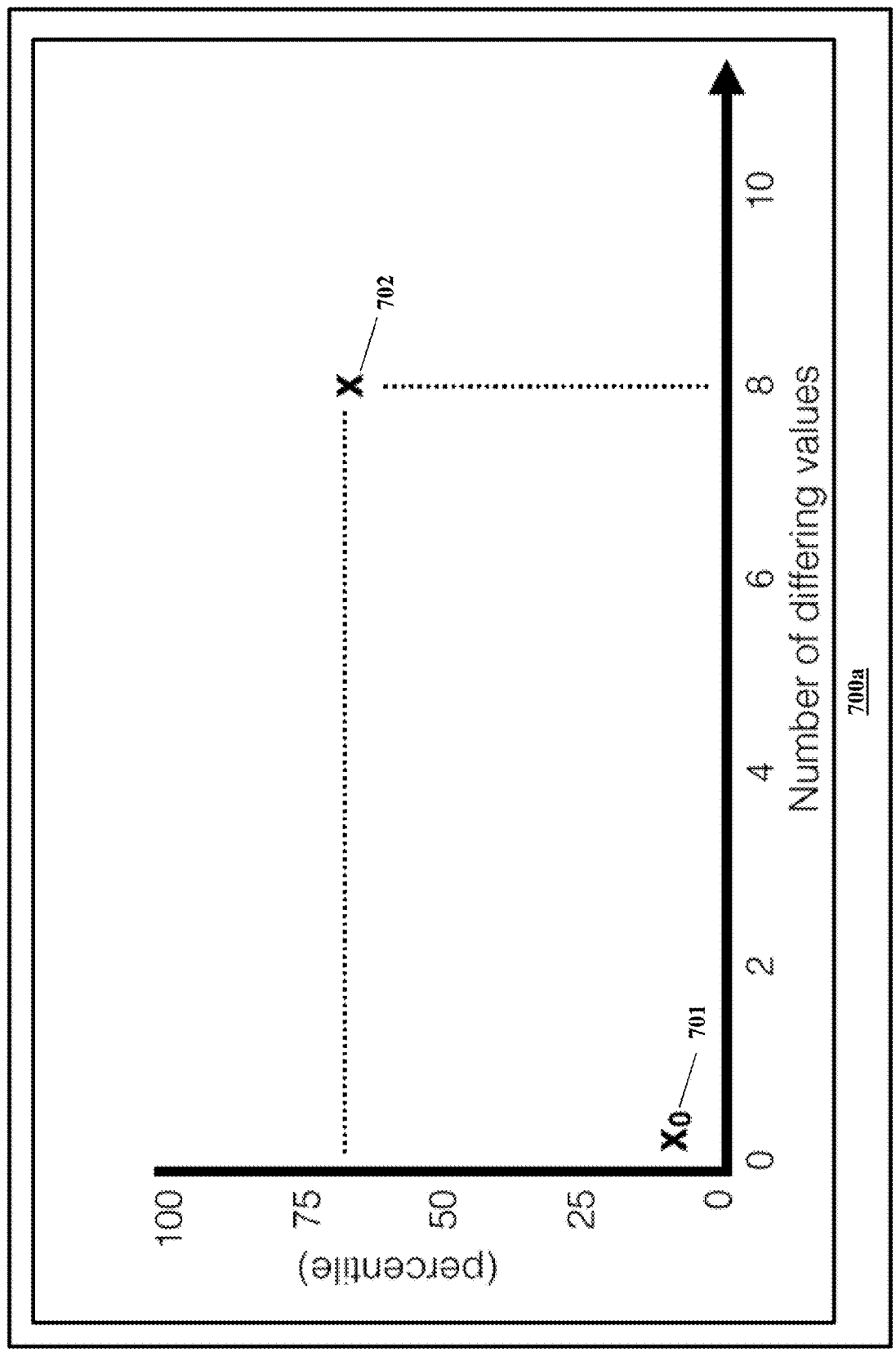
FIG. 7A shows a fourth exemplary GUI, according to an exemplary embodiment.
Figure 7B:
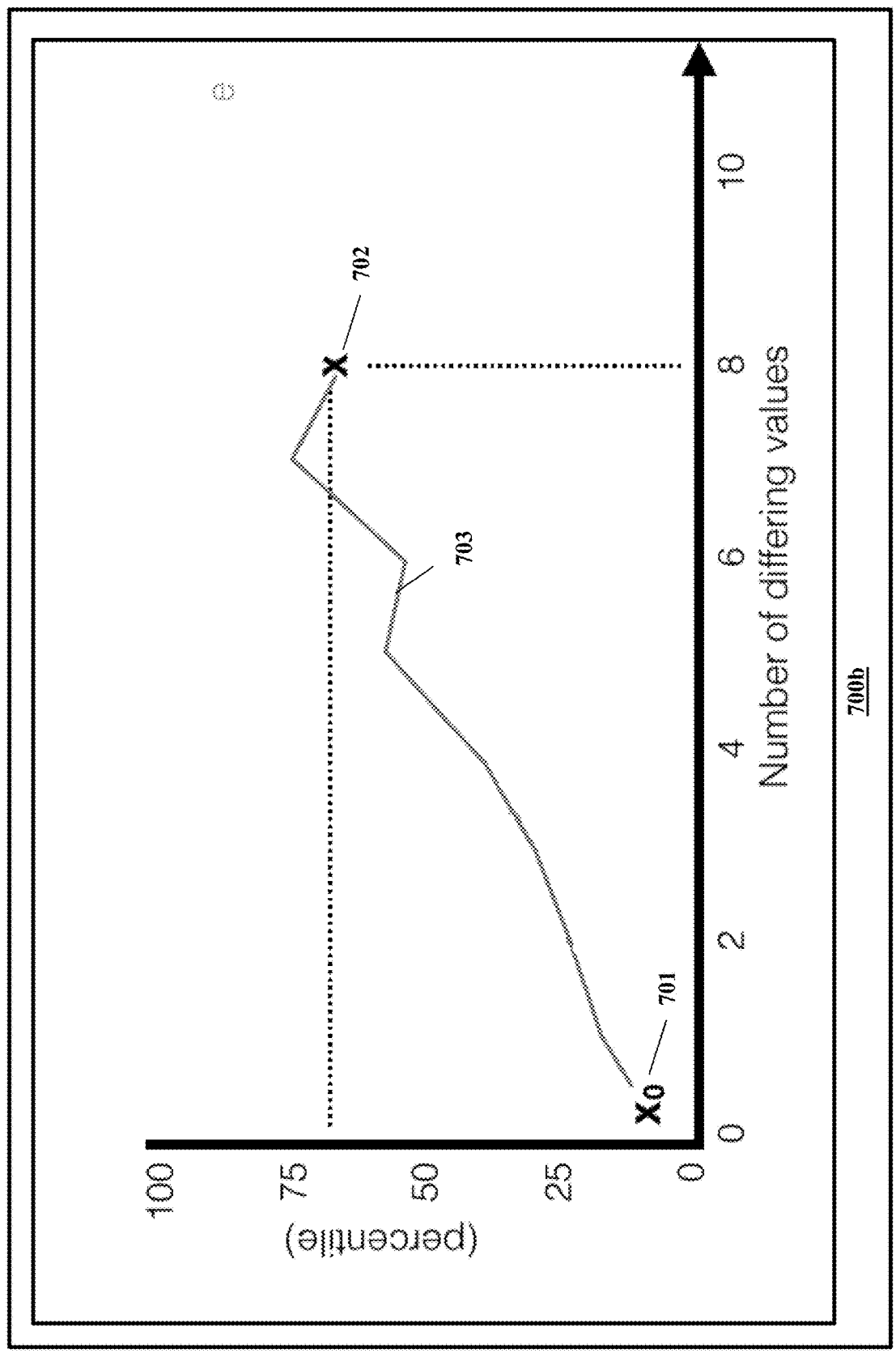
FIG. 7B shows a fifth exemplary GUI, according to an exemplary embodiment.

FIG. 7A shows an exemplary GUI 700a displaying the relative graphical locations of a baseline reference profile 701 and the user profile 702 of a general user. FIG. 7B shows an updated GUI 700b displaying a stepwise perturbation from the reference profile 701 to the user profile 702. An exemplary step has been labeled as 703.

Figure 8A:
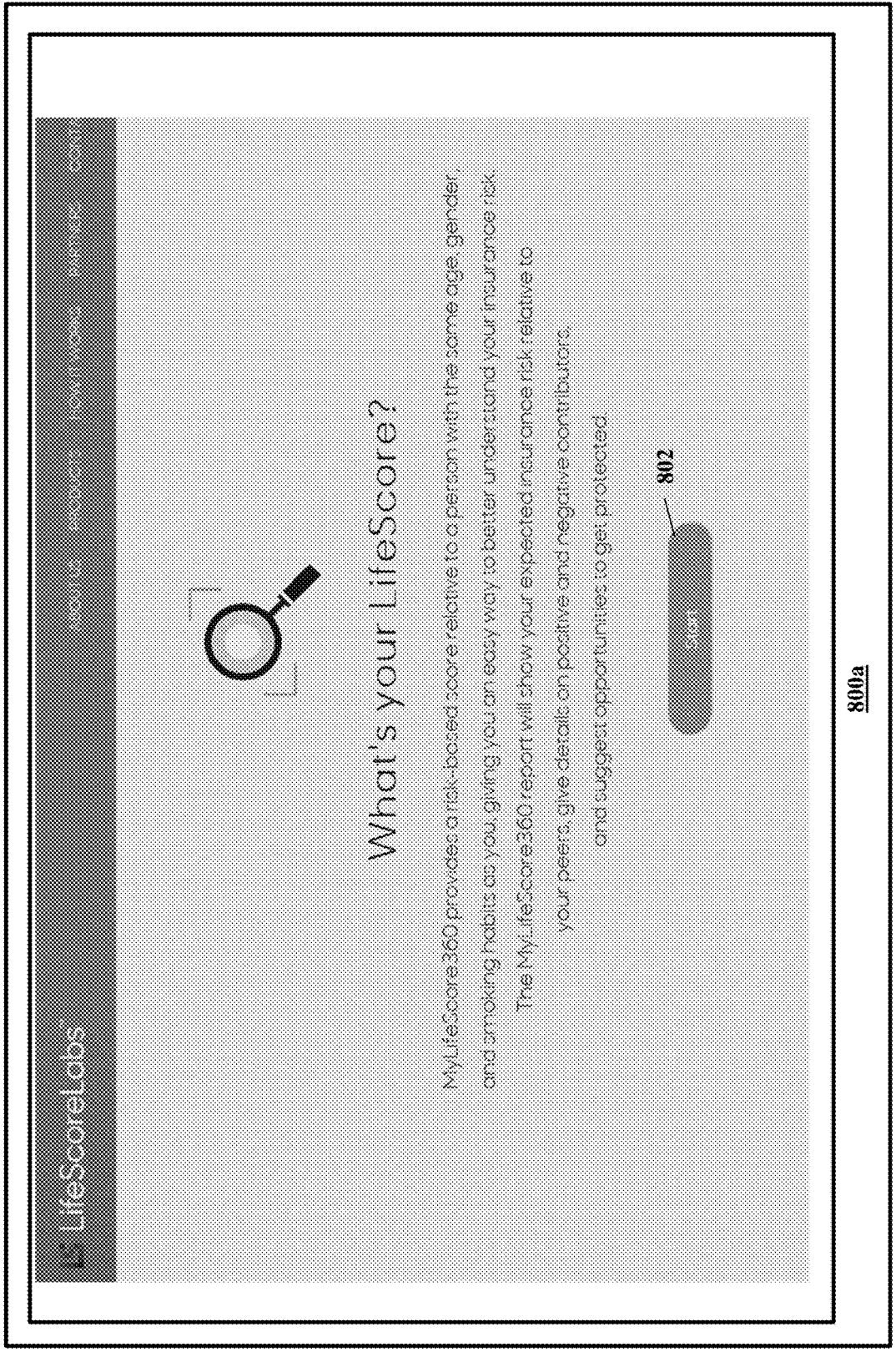
FIGS. 8A-8O show exemplary GUIs for a general user, according to an exemplary embodiment.

FIGS. 8A-8O show illustrative consumer facing GUIs 800a-800o (collectively or commonly referred to as 800), according to an embodiment. A computer (e.g., a server) may generate the consumer facing GUIs 800 to be displayed as various webpages in a browser environment. In addition or in the alternative, the computer (e.g., a smartphone) may generate the GUIs as multiple interactive interfaces within a mobile application. The illustrative GUIs 800 may enable a user to enter vital data and receive granular risk scores based upon the vital data. The GUIs 800 may also allow the user to dynamically change the vital data and dynamically receive update risk scores based on the changed data. Through the GUIs 800, the user may have access to the underlying machine learning model used to generate the risk scores.

FIG. 8A shows an illustrative GUI 800a which the computer may generate when the user first executes a risk scoring program. The program may be a web-based program running on a server and the GUI 800a may be displayed on a browser. Alternatively, the program may be a standalone application (e.g., mobile application) on a mobile phone and the GUI 800a may be displayed by the mobile application. As shown, the GUI 800a may include a start button 802 for the user to enter or update data to receive a risk score.

Figure 8B:
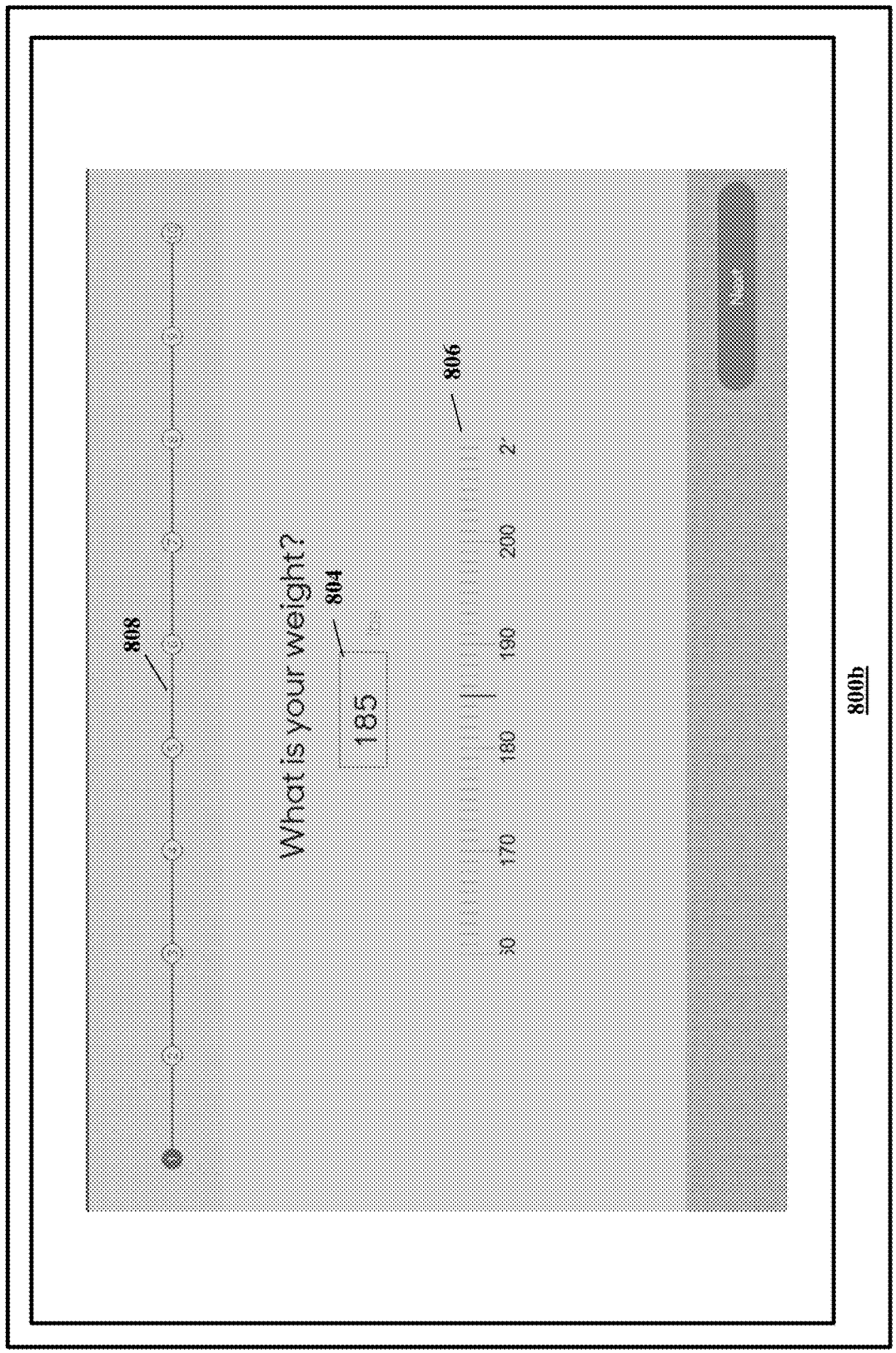

FIG. 8B shows an illustrative GUI 800b for the user to user to enter the weight. The GUI 800b may include data field 804 for the user to enter weight. The GUI 800b may further include a graphical scale 806 for the user to select the weight. It is to be understood that the user may use either the data field 804 or the graphical scale 806 to enter or update the age. Furthermore, the computer may automatically update the graphical scale 806 in response to the user entering the weight in the data field 804 and vice versa. A progress bar 808 may indicate the progress of (or the steps of) of the data entry through the GUIs 800. As shown by the progress bar, GUI 800b may be associated with step 1 of the data entry through the GUIs 800.

Figure 8C:
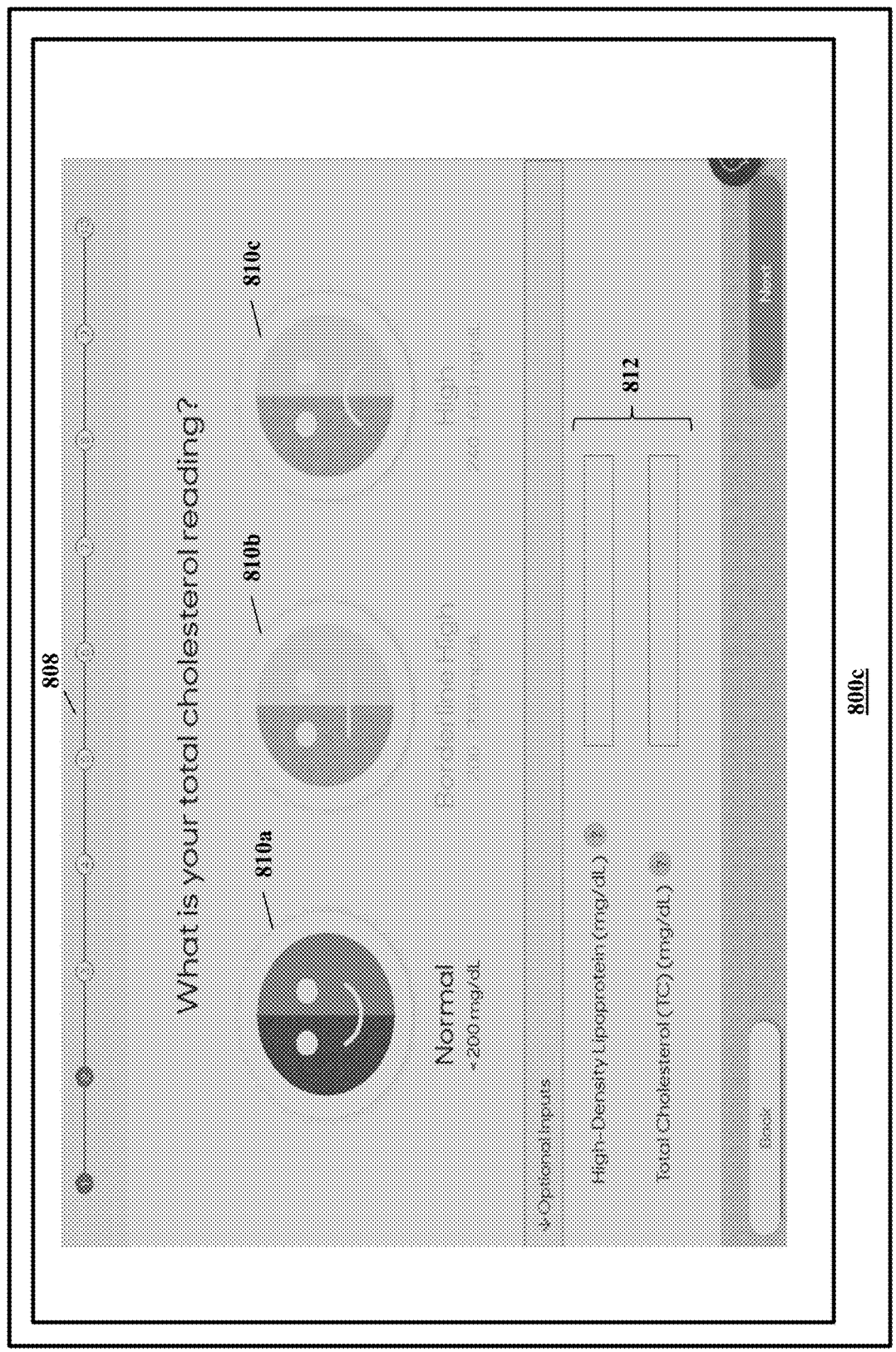

FIG. 8C shows an illustrative GUI 800c for the user to enter cholesterol reading. For example, the GUI 800c may display selectable options 810a, 810b, 810c. Selectable option 810a may be associated with normal cholesterol level, selectable option 810b may be associated with borderline high cholesterol level, and selectable option 810c may be associated with high cholesterol level. In addition to the selectable options 810a, 810b, 810c, the GUI 800c may also provide an interface 812 for optional inputs. As shown, the optional inputs may be the readings for High-Density Lipoprotein (HDL) and Total Cholesterol (TC). Within the GUI 800c, the progress bar 808 may indicate that the GUI 800c is associated with step 2 of the data entry process.

Figure 8D:
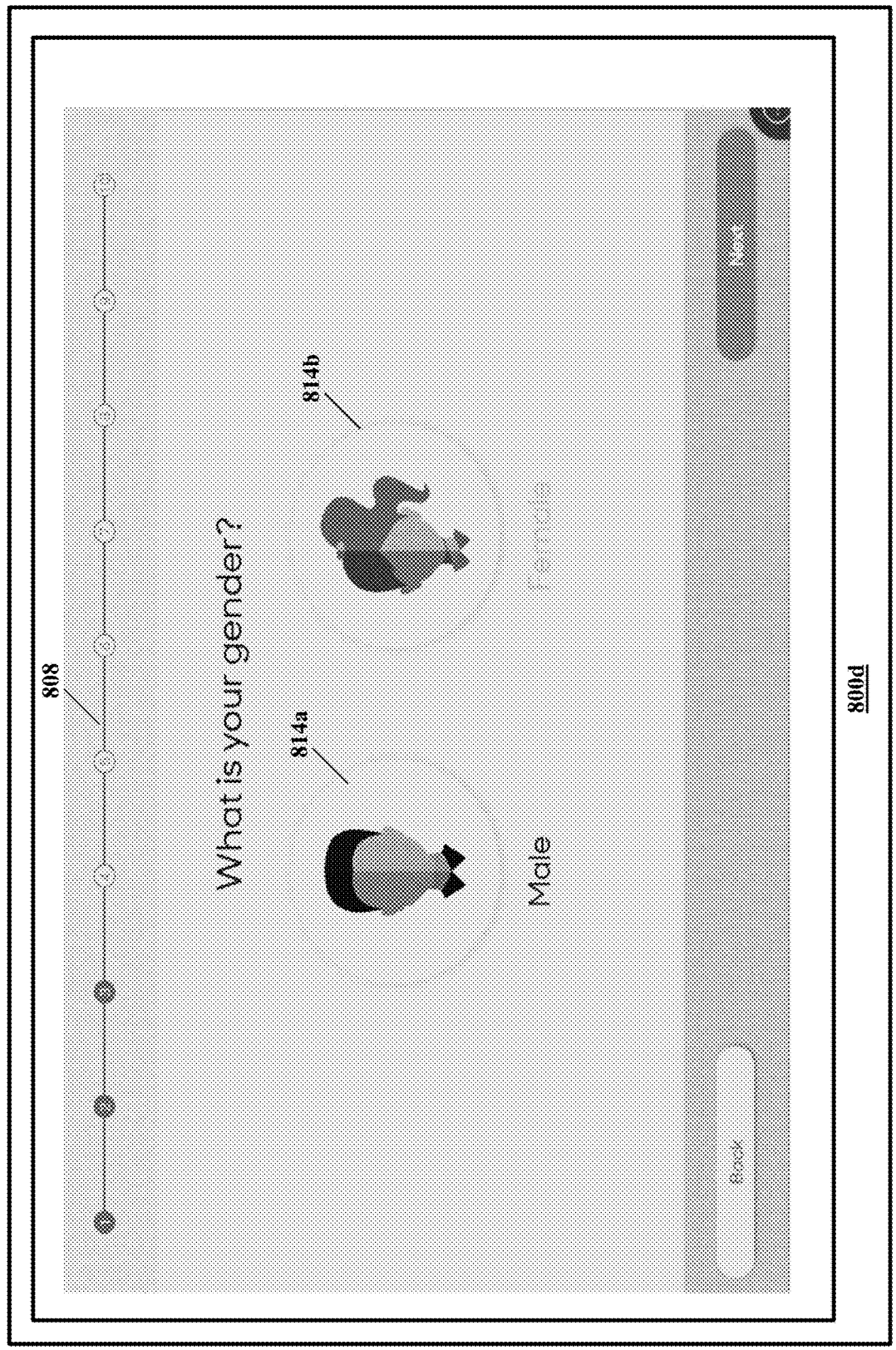

FIG. 8D shows an illustrative GUI 800d for the user to enter his or her gender. As shown, the GUI 800d may display selectable options 814a, 814b to enter the user's gender. Selectable option 814a may correspond to the user being male and selectable option 814b may correspond to the user being female. Within the GUI 800d, the progress bar 808 may indicate that the GUI 800c is associated with step 3 of the date entry process.

Figure 8E:
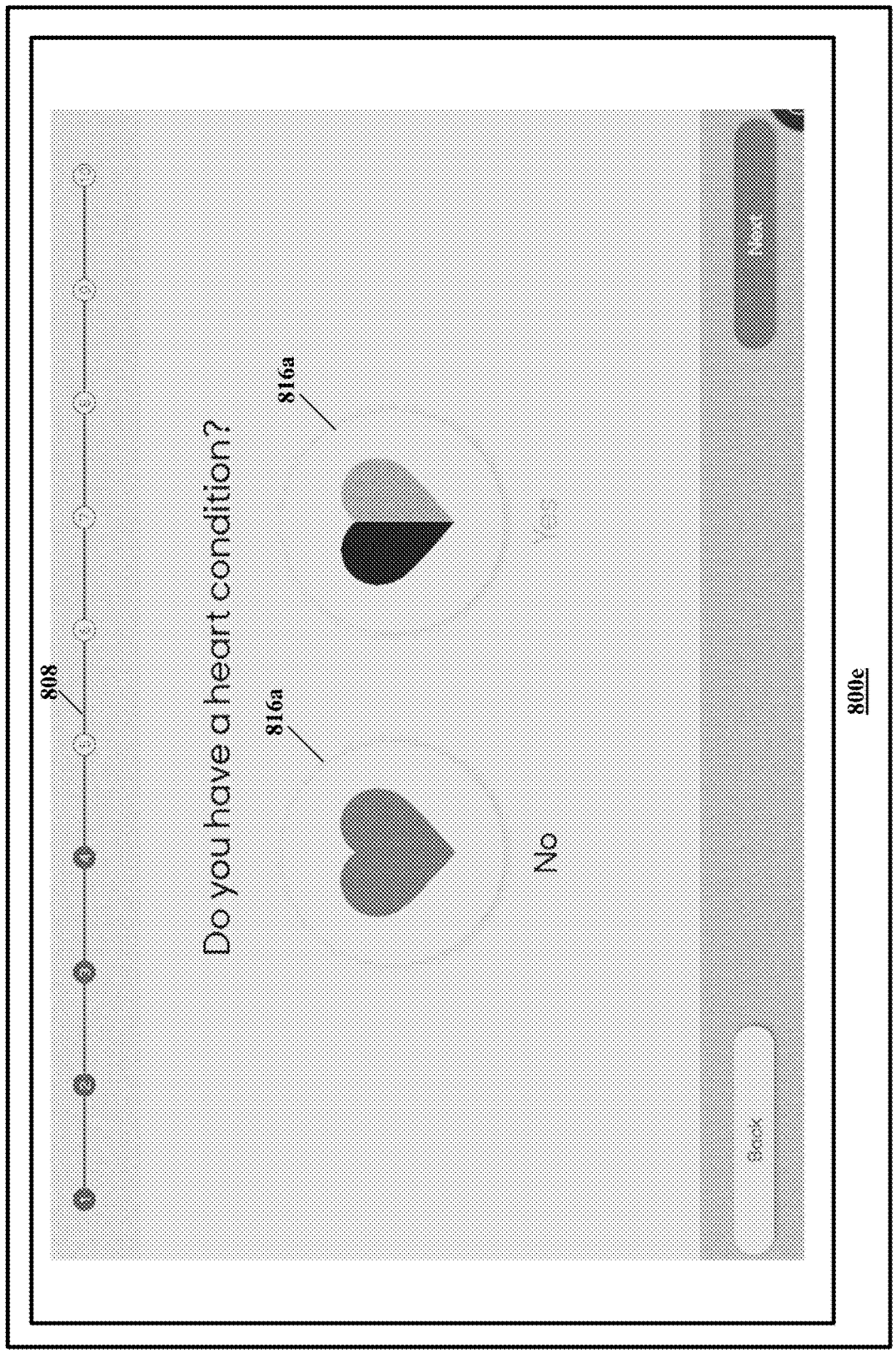

FIG. 8E shows an illustrative GUI 800e for the user to indicate if the user has a heart condition. As shown, the GUI 800e may display selectable options 816a, 816b. Selectable option 816a may be correspond to the user not having a heart condition and selectable option 816b may correspond to the user having a heart condition. Within the GUI 800e, the progress bar 808 may indicate the GUI 800c is associated with step 4 of the data entry process.

Figure 8F:
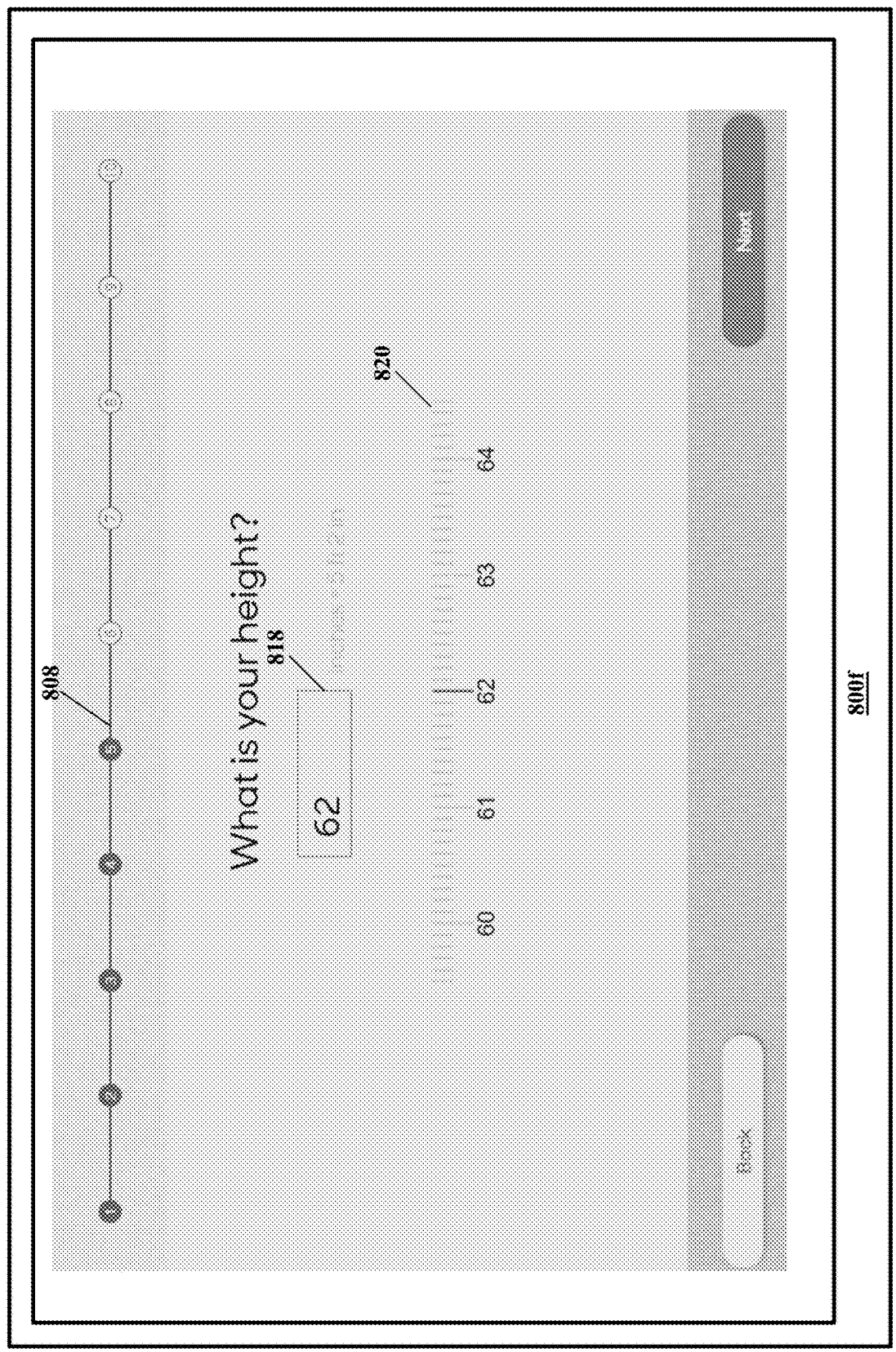

FIG. 8F shows an illustrative GUI 800e for the user to enter his or her height. To that end, the GUI 800e may display a data field 818 for the user to type the height (e.g., in inches). The GUI 800e may further display a graphical scale 820 for the user to select a height. The user may use either the data field 810 or the graphical scale 820 to enter the height. It should be understood that the computer may automatically update the graphical scale 820 in response to the user entering the height in the data field 810 and vice versa. Within the GUI 800f, the progress bar 808 may indicate that the GUI 800f is associated with step 5 of the data entry process.

Figure 8G:
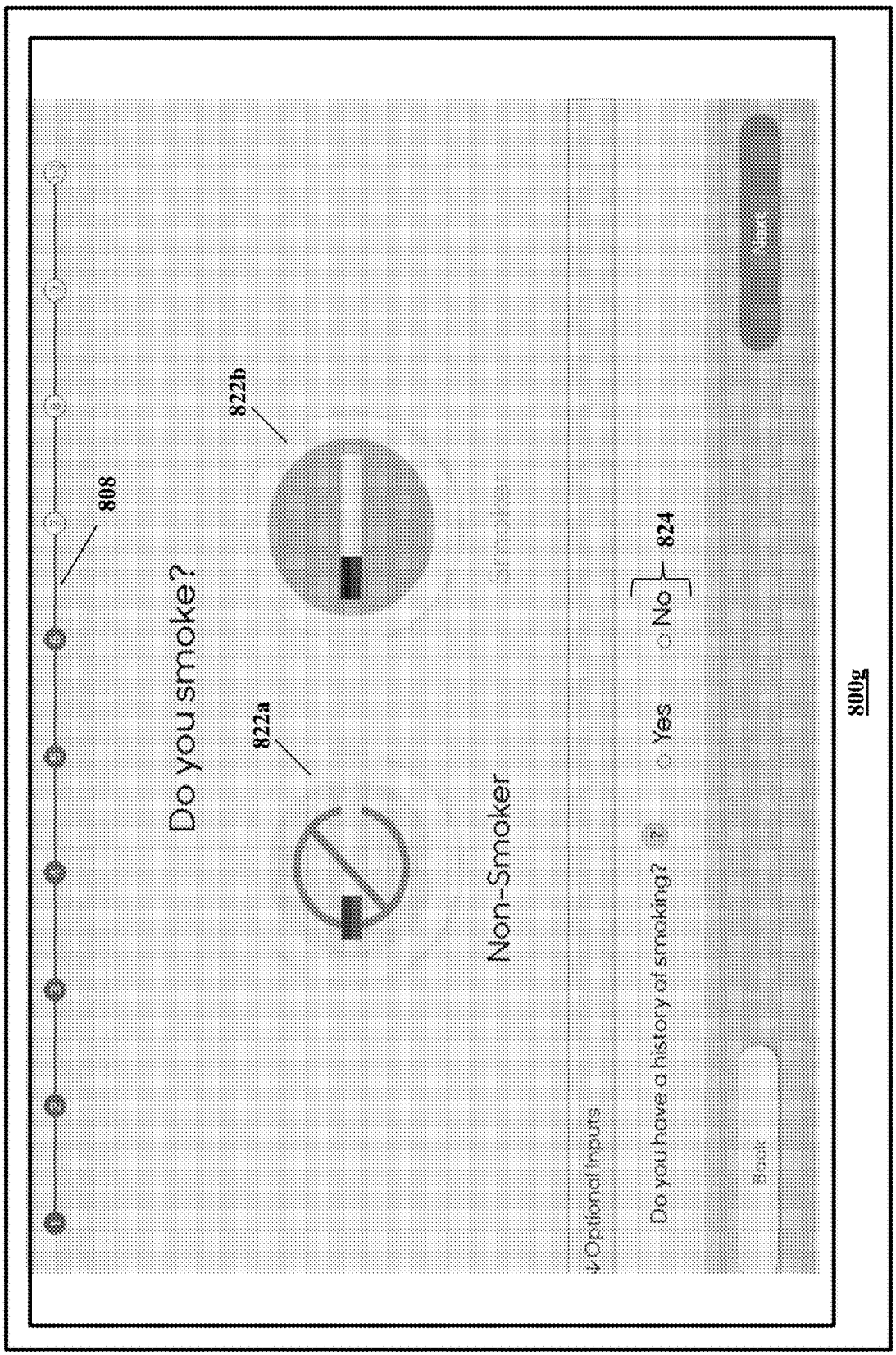

FIG. 8G shows an illustrative GUI 800f for the user to indicate whether the user smokes. To that end, the GUI 800g may display selectable options 822a, 822b. Selectable option 822a may correspond to the user being a non-smoker and selectable option 822b may correspond to the user being a smoker. The GUI 800f may further provide an interface 824 for optional inputs. As shown, the interface 824 may allow the user to enter whether the user has a history of smoking. Within the GUI 800g, the progress bar 808 may indicate that the GUI 800g is associated with step 6 of the data entry process.

Figure 8H:
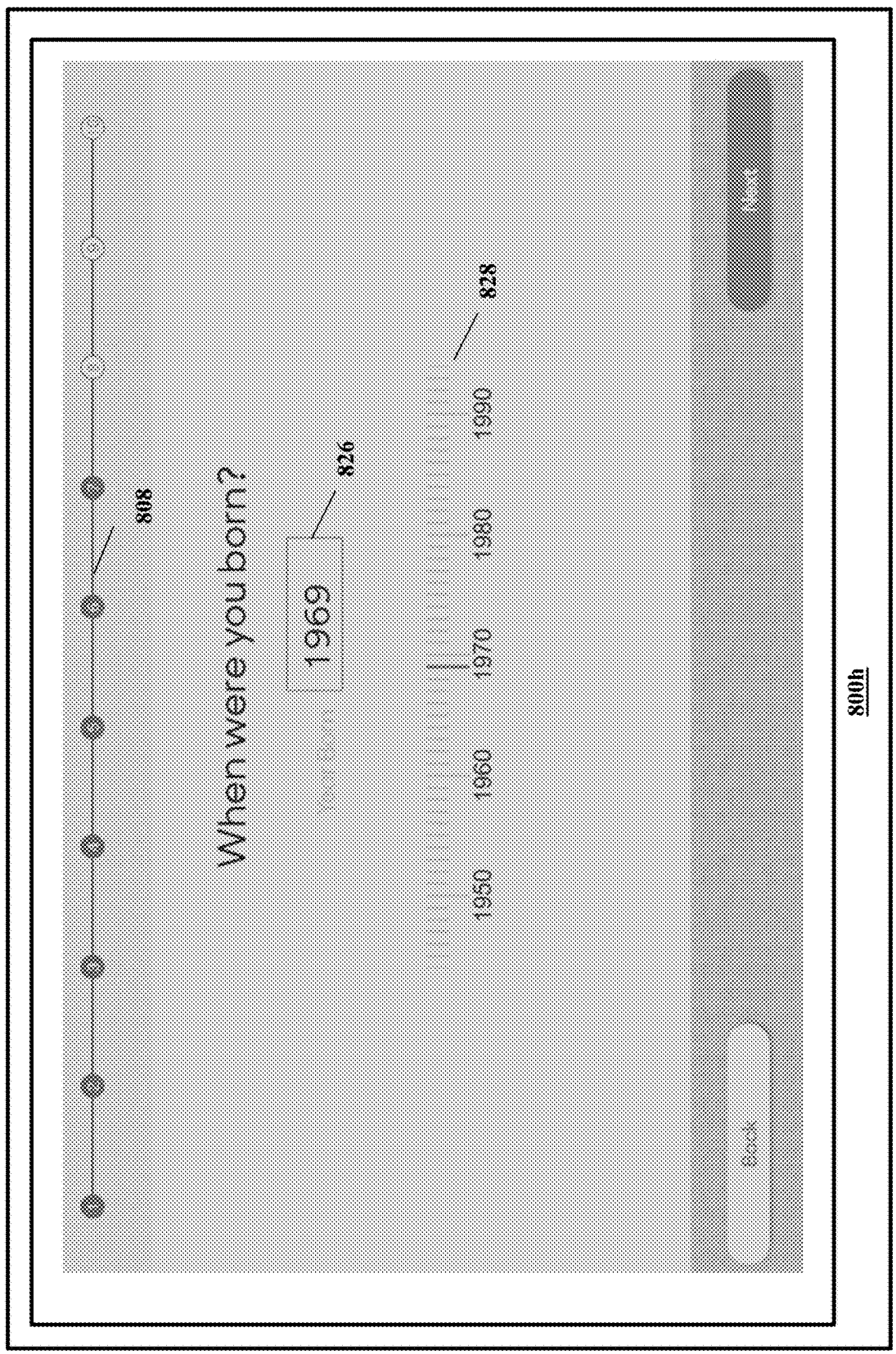

FIG. 8H shows an illustrative GUI 800h for the user to enter the user's birth year. To that end, the GUI 800h may display a data field 826 for the user to type in the user's birth year. The GUI 800h may also display a graphical scale 828 for the user to select the user's birth year. It should be understood that the computer may automatically update the graphical scale 828 in response to the user keying in the information or updating the information in the data field 826 and vice versa. Within the GUI 800h, the progress bar 808 may indicate that the GUI 800h is associated with step 7 of the data entry process.

Figure 8I:
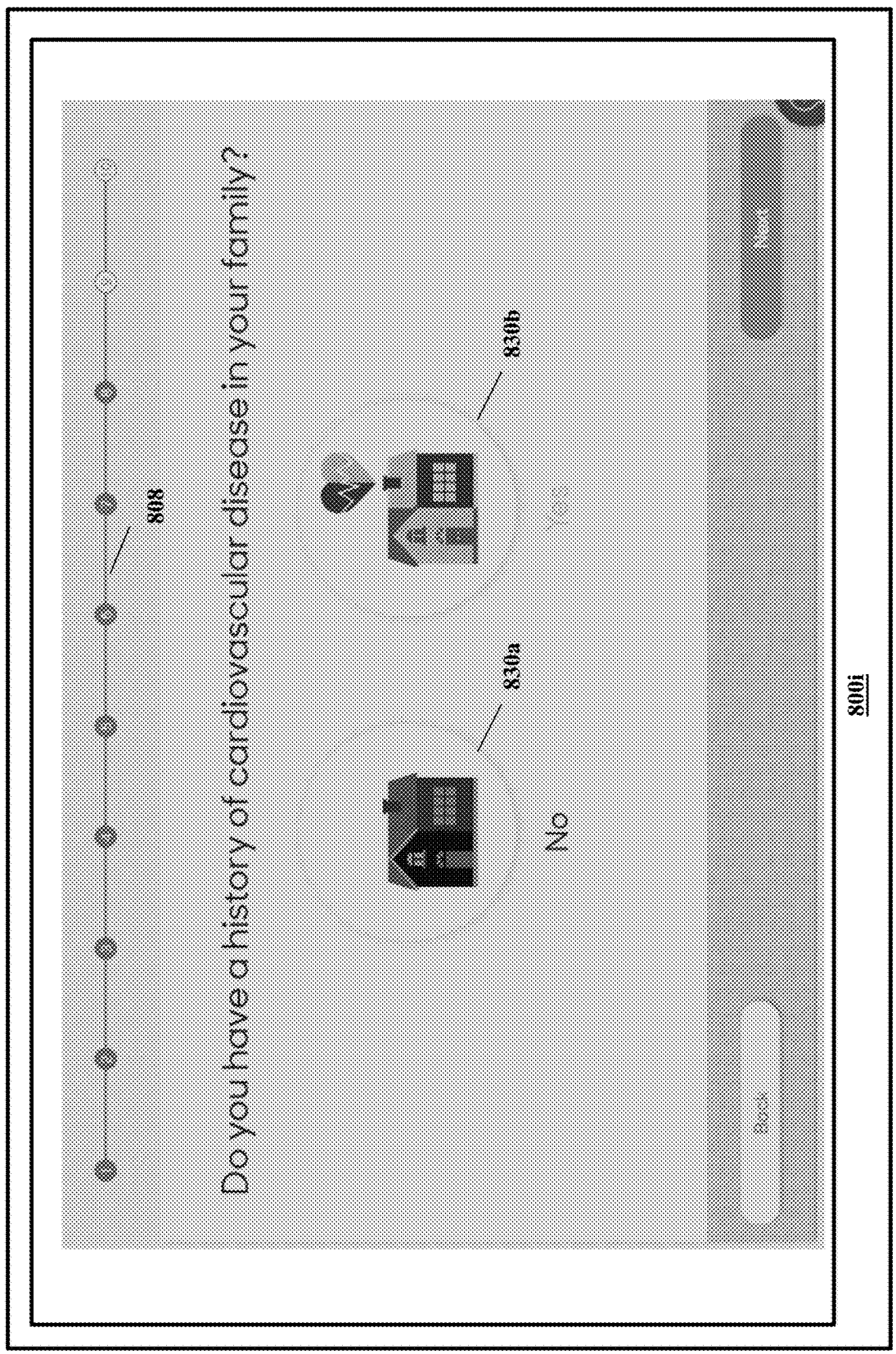

FIG. 8I shows an illustrative GUI 800i for the user to indicate whether there is a history of cardiovascular disease in the user's family. For example, GUI 800i may display selectable options 830a, 830b. Selectable option 830a may correspond to the user not having a history of cardiovascular disease in the family and selectable option 830b may correspond to the user having a history of cardiovascular disease in the family. Within the GUI 800i, the progress bar 808 may indicate that the GUI 800i is associated with step 8 of the data entry process.

Figure 8J:
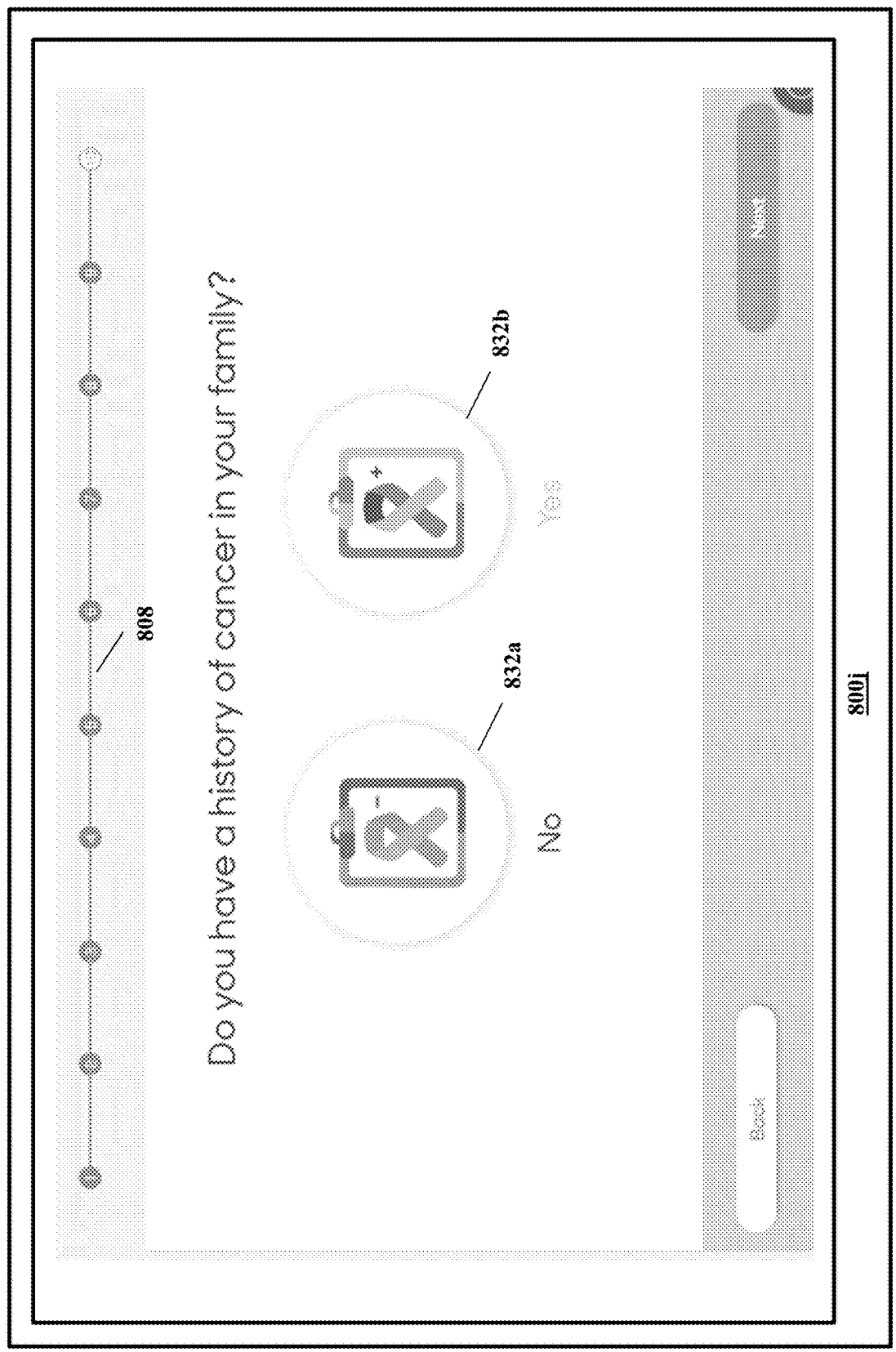

FIG. 8J shows an illustrative GUI 800j for the user to indicate whether there is a history of cancer in the family. To that end, the GUI 800j may display selectable options 832a, 832b. Selectable option 832a may correspond to the user not having a history of cancer in the family and selectable option 832b may correspond to the user having a history of cancer in the family. Within the GUI 800j, the progress bar 808 may indicate that the GUI 800j may be associated with step 9 of the data entry process.

Figure 8K:
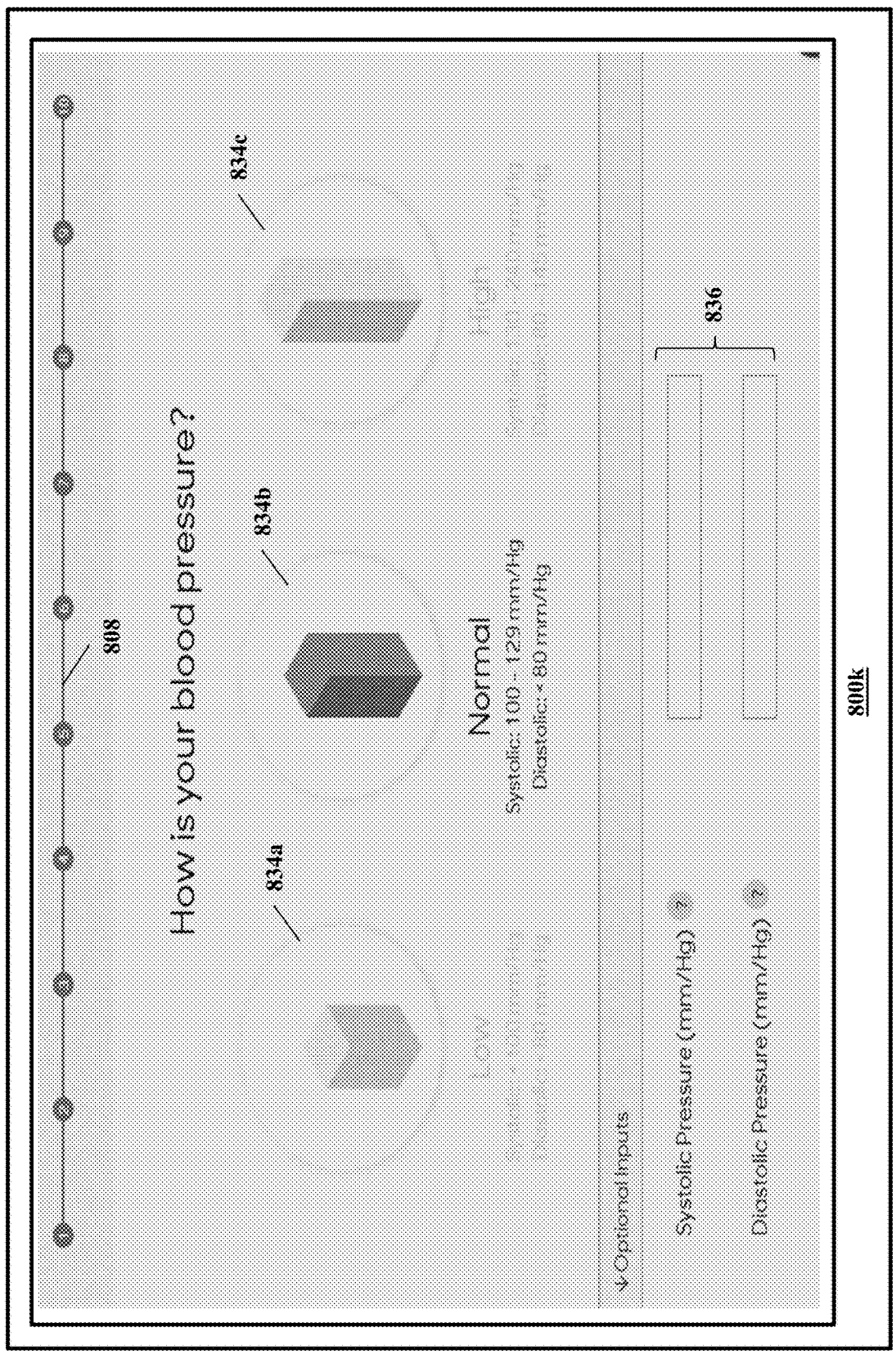

FIG. 8K shows an illustrative GUI 800k for the user indicate the user's blood pressure level. To that end, the GUI 800k may display selectable options 834a, 834b, 834c. Selectable option 834a may correspond to the user having a low blood pressure; selectable option 834b may correspond to the user having a normal blood pressure; and selectable option 834c may correspond to the user having a high blood pressure. The GUI 800k may further display an optional interface 836 for the user to enter optional inputs. For example, the optional inputs may be systolic pressure and the diastolic pressure of the user. Within the GUI 800k, the progress bar 808 may indicate that the GUI 800k may be associated with step 10 of the data entry process.

Figure 8L:
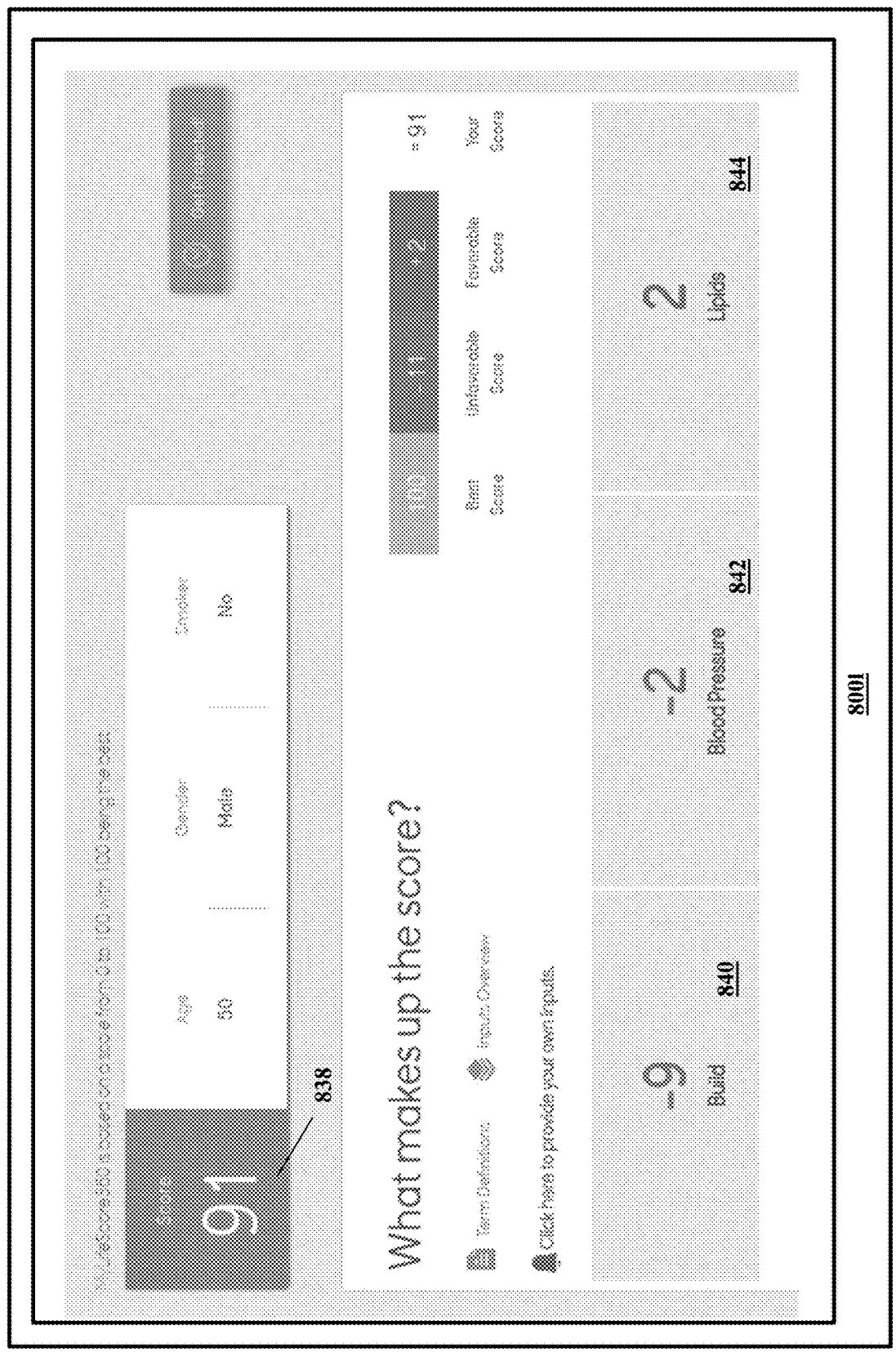

FIG. 8L shows an illustrative GUI 800l displaying a risk score 838 generated by back end machine learning model based on the inputs received form the user in the previous GUIs 800a-800k. In addition to the risk score 838, the GUI 800l may also display the one or more contributing factors to the risk score 838. The illustrative contributing factors shown in the GUI 800l are build 840, blood pressure 842b, and lipids 844. As shown, the build 840 and the blood pressure 842 may have negatively impacted the risk score 838 and the lipids 844 may have positively impacted the risk score 838. The computer may also provide more granular details of the how the factors 840, 842, 844 contributed to the risk score 838 and may allow the user to generate "what-if" scenarios by enabling a dynamic updates to the inputs associated with the factors 840, 842, 844.

Figure 8M:
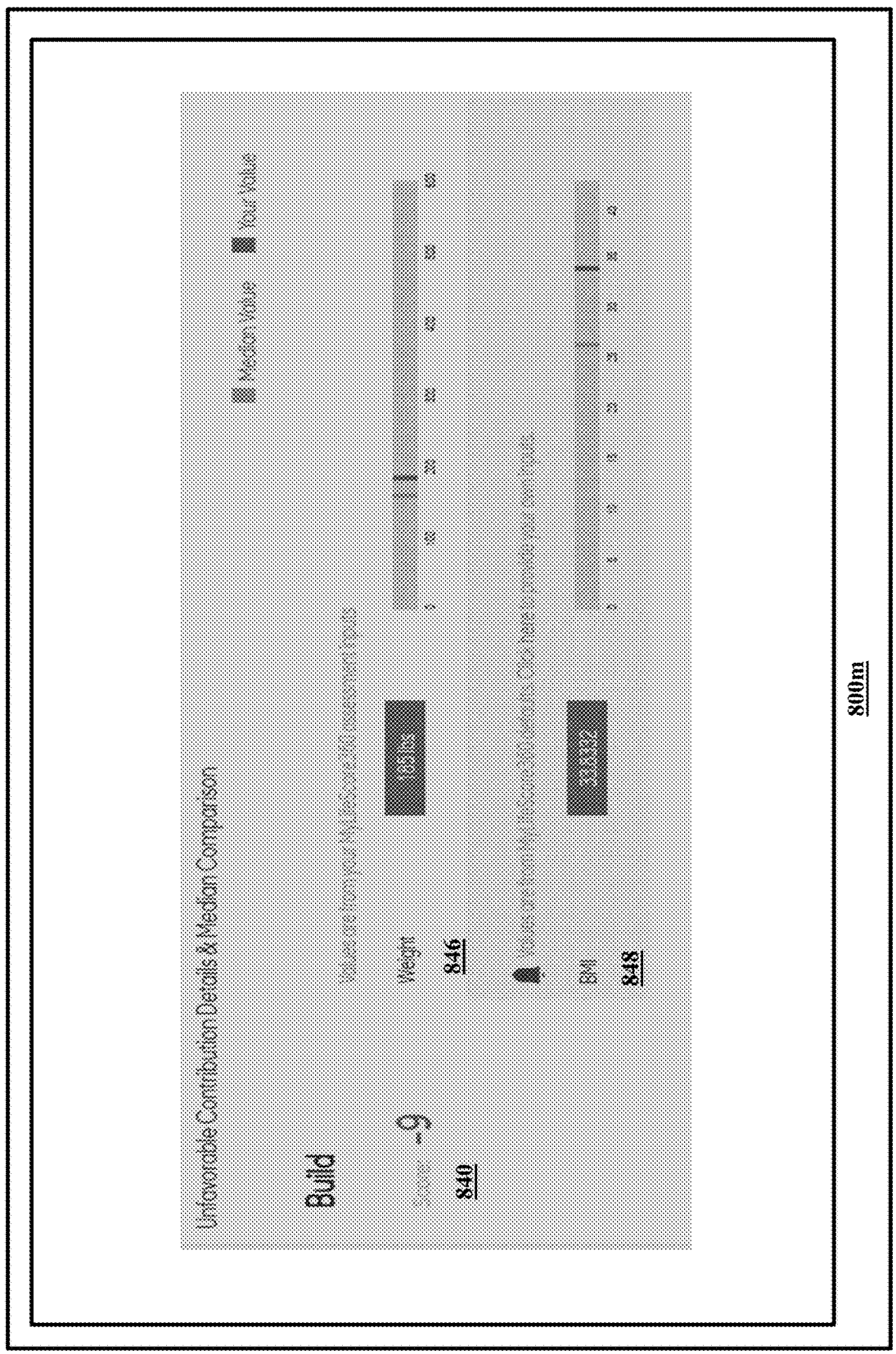

For instance, FIG. 8M shows an illustrative GUI 800m with granular details of the build factor 840. As shown, the inputs for the build factor 840 include weight 846 and body mass index (BMI) 848. For each of the weight 846 and BMI 848, the GUI 800m may display a scale with the median value and the user's value. The user may dynamically edit these inputs (e.g., change the BMI) and the computer may dynamically update the GUI 800m to display to show an updated score. For example, the computer may update the shown score −9 to another score based upon the changed in one or more of the weight 846 and the BMI 848.

Figure 8N:
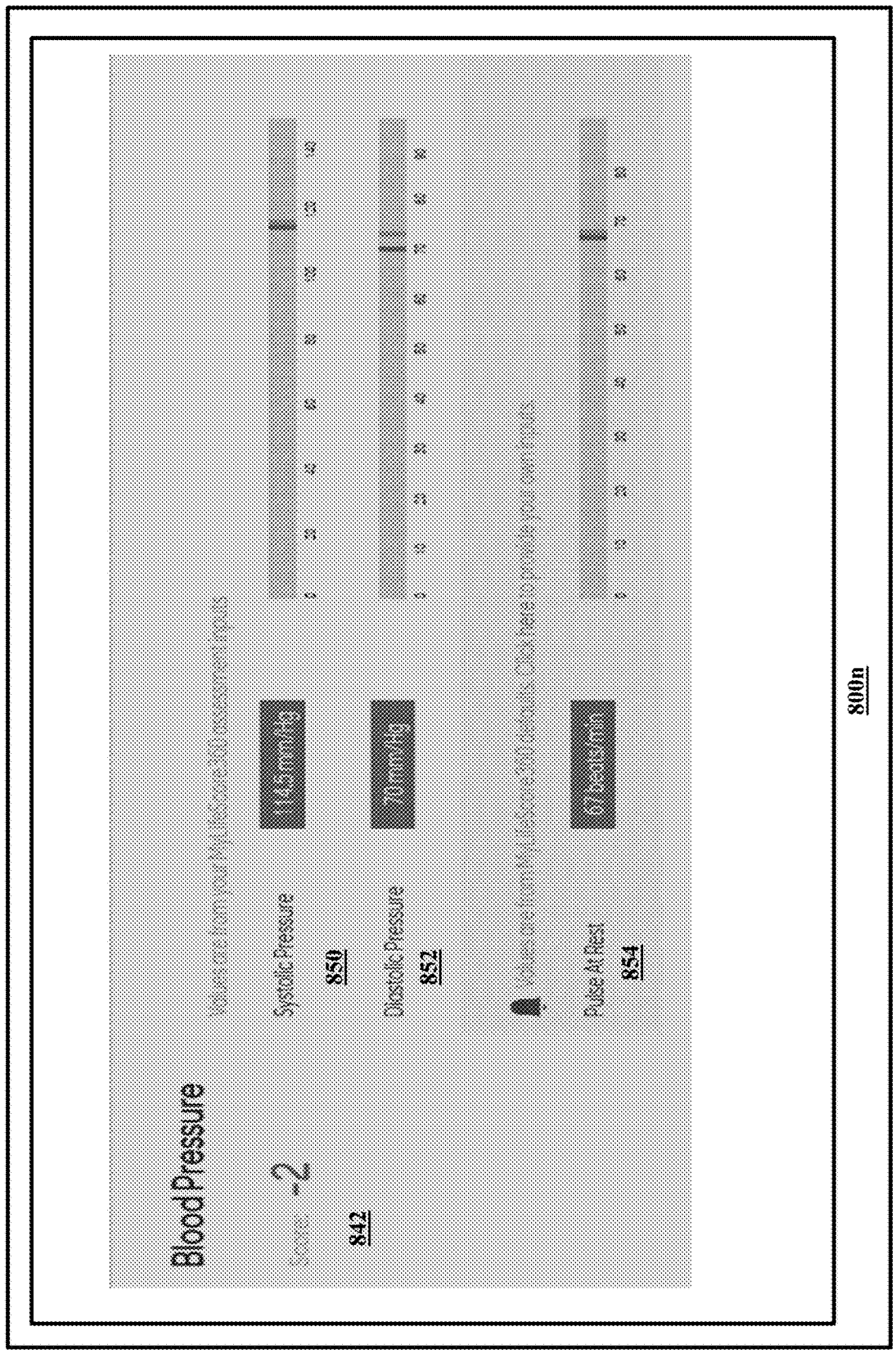
Figure 80:
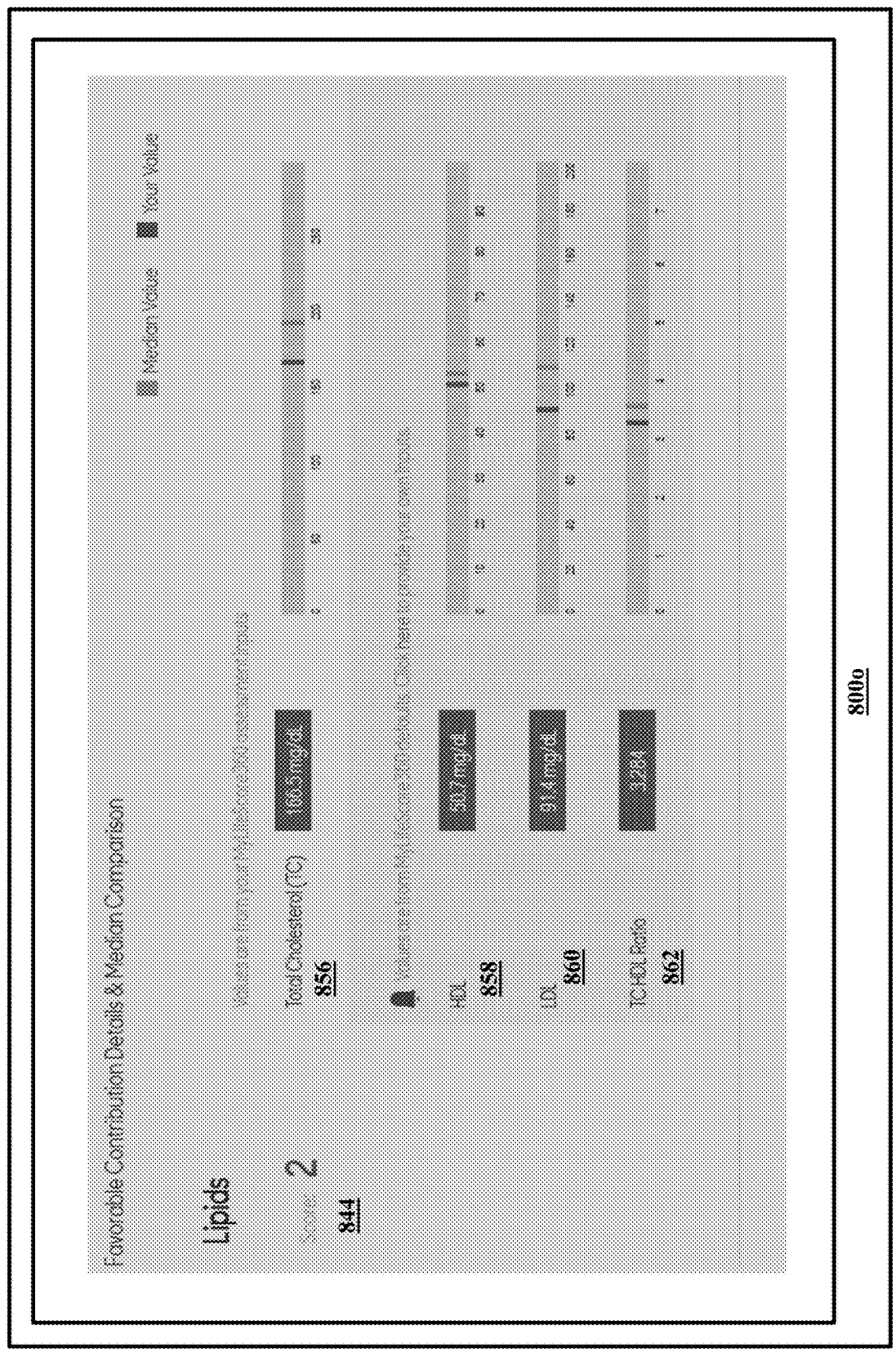

FIG. 8N shows an illustrative GUI 800n with granular details for the blood pressure 842 factor. Within the GUI 800n, the computer may display a score indicating the contribution of the blood pressure factor 842 to the risk score 838 (shown as −2). As shown, the inputs associated with the blood pressure factor 842 may include systolic pressure 850, diastolic pressure 852, and pulse at test 854. For each of the inputs 850, 852, 854, the GUI 800n may include a scale, a median value, and the user's value. The GUI 800n may dynamically display an updated score in response to the user dynamically changing one or more of the inputs 850, 852, 854.

FIG. 8O shows an illustrative GUI 800o with granular details of the lipids factor 844. Within the GUI 800o, the computer may display a score indicating the contribution of the lipids factor 844 to the risk score (shown as 2). As shown, the inputs associated with the lipids factor 844 may include total cholesterol (TC) 856, high-density lipoproteins (HDL) 858, low-density lipoproteins (LDL) 860, and TC to HDL ratio 862. For each of the inputs 856, 858, 860, 862, the GUI 800o may include a scale, a median value, and the user's value. The GUI 800n may dynamically display an updated score in response to the user dynamically changing one or more of the inputs 856, 858, 860, 862.

Therefore, the GUIs 800 as a consumer facing tool may allow a user to dynamically input vital data to the computer and receive a risk score in real time. The GUIs 800 may provide a visual feedback as to the contribution of various inputs to the overall risk score 838. The user may dynamically change one or more input values (e.g., to create "what-ifs" scenarios) and receive real-time feedback as to how the risk score changes based on the changed input values. Therefore, the GUIs 800 enable a general user to access the back-end machine learning model to generate risk scores for multiple scenarios.

The foregoing method descriptions and the process flow diagrams are provided merely as illustrative examples and are not intended to require or imply that the steps of the various embodiments must be performed in the order presented. The steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, and the like. When a process corresponds to a function, the process termination may correspond to a return of the function to a calling function or a main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the generic principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A computer-implemented method, comprising:
retrieving, by a processor, a baseline set of factors corresponding to a baseline population of a plurality of users to which a user belongs, the baseline population comprising at least one attribute in common with the user;
executing, by the processor, an artificial intelligence model to predict a score for the user, wherein the artificial intelligence model is iteratively executed over the baseline set of factors and a plurality of factors associated with the user, wherein the artificial intelligence model replaces a baseline factor of the baseline set of factors with a corresponding factor of the plurality of factors associated with the user and generates an output corresponding to a contribution of the corresponding factor to the score;

presenting, by the processor, for display on a user interface:
- a first set of bars stretching in a first direction from a zero-line, wherein each bar in the first set of bars indicates a respective negative factor of the plurality of factors associated with the user that is negatively contributing to the score, a length of each bar indicating a magnitude of negative contribution of the respective negative factor;
- a second set of bars stretching in a second direction from the zero-line, wherein each bar in the second set of bars indicates a respective positive factor of the plurality of factors associated with the user that is positively contributing to the score, a length of each bar indicating a magnitude of positive contribution of the respective positive factor; and
- in response to the processor receiving a selection of a bar within the first and second set of bars, dynamically revising, by the processor, the user interface to display a user attribute corresponding to a factor indicated by the selected bar.

2. The method of claim 1, wherein the user interface further comprises an identification of the artificial intelligence model used to generate the score of the user.

3. The method of claim 1, wherein the artificial intelligence model uses at least one of a weight, cholesterol level, gender, height, age, family history, or blood pressure to calculate the score.

4. The method of claim 1, wherein the user interface further comprises a histogram showing a distribution of scores of the plurality of users, wherein the score of the user is juxtaposed in the histogram.

5. The method of claim 1, wherein the user interface further comprises a histogram showing a percentile distribution of the score of the plurality of users, wherein the percentile distribution of the score of the user is juxtaposed on the histogram.

6. The method of claim 1, wherein the user interface further comprises a score class of the user.

7. The method of claim 1, wherein the plurality of users corresponds to users in a same score class as the user.

8. The method of claim 1, wherein the plurality of users corresponds to users in a different score class from the user.

9. The method of claim 1, wherein the score corresponds to a mortality risk.

10. The method of claim 1, wherein the artificial intelligence model is selected based on the at least one attribute of the user.

11. A computer system comprising:
- a server comprising a processor and a non-transitory computer-readable medium containing instructions that when executed by the processor causes the processor to perform operations comprising:
- retrieve a baseline set of factors corresponding to a baseline population of a plurality of users to which a user belongs, the baseline population comprising at least one attribute in common with the user;
- execute an artificial intelligence model to predict a score for the user, wherein the artificial intelligence model is iteratively executed over the baseline set of factors and a plurality of factors associated with the user, wherein the artificial intelligence model replaces a baseline factor of the baseline set of factors with a corresponding factor of the plurality of factors associated with the user and generates an output corresponding to a contribution of the corresponding factor to the score;
- present for display on a user interface:
- a first set of bars stretching in a first direction from a zero-line, wherein each bar in the first set of bars indicates a respective negative factor of the plurality of factors associated with the user that is negatively contributing to the score, a length of each bar indicating a magnitude of negative contribution of the respective negative factor;
- a second set of bars stretching in a second direction from the zero-line, wherein each bar in the second set of bars indicates a respective positive factor of the plurality of factors associated with the user that is positively contributing to the score, a length of each bar indicating a magnitude of positive contribution of the respective positive factor; and in response to the processor receiving a selection of a bar within the first and second set of
- bars, dynamically revise the user interface to display a user attribute corresponding to a factor indicated by the selected bar.

12. The system of claim 11, wherein the user interface further comprises an identification of the artificial intelligence model used to generate the score of the user.

13. The system of claim 11, wherein the artificial intelligence model uses at least one of a weight, cholesterol level, gender, height, age, family history, or blood pressure to calculate the score.

14. The system of claim 11, wherein the user interface further comprises a histogram showing a distribution of scores of the plurality of users, wherein the score of the user is juxtaposed in the histogram.

15. The system of claim 11, wherein the user interface further comprises a histogram showing a percentile distribution of the score of the plurality of users, wherein the percentile distribution of the score of the user is juxtaposed on the histogram.

16. The system of claim 11, wherein the user interface further comprises a score class of the user.

17. The system of claim 11, wherein the plurality of users corresponds to users in the same score class as the user.

18. The system of claim 11, wherein the plurality of users corresponds to users in a different score class from the user.

19. The system of claim 11, wherein the score corresponds to a mortality risk.

20. The system of claim 11, wherein the artificial intelligence model is selected based on the at least one attribute of the user.

* * * * *